(12) United States Patent
Cicciarelli et al.

(10) Patent No.: US 10,167,486 B2
(45) Date of Patent: *Jan. 1, 2019

(54) VECTORS AND METHODS FOR LONG-TERM IMMUNE EVASION TO PROLONG TRANSPLANT VIABILITY

(71) Applicant: National Institute of Transplantation Foundation, Los Angeles, CA (US)

(72) Inventors: James C. Cicciarelli, Rolling Hills, CA (US); Noriyuki Kasahara, Los Angeles, CA (US); Christopher R. Logg, South Pasedena, CA (US)

(73) Assignee: NATIONAL INSTITUTE OF TRANSPLANTATION FOUNDATION, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/621,880

(22) Filed: Jun. 13, 2017

(65) Prior Publication Data

US 2018/0127779 A1 May 10, 2018

Related U.S. Application Data

(63) Continuation of application No. 13/567,064, filed on Aug. 5, 2012, now Pat. No. 9,677,087, which is a continuation of application No. 11/131,507, filed on May 18, 2005, now Pat. No. 8,236,771.

(60) Provisional application No. 60/571,873, filed on May 18, 2004.

(51) Int. Cl.
*C12N 15/113* (2010.01)
*C12N 15/86* (2006.01)
*A61K 39/00* (2006.01)

(52) U.S. Cl.
CPC ............ *C12N 15/86* (2013.01); *A61K 39/001* (2013.01); *A61K 2039/5156* (2013.01); *A61K 2039/525* (2013.01); *A61K 2039/5256* (2013.01); *C12N 2740/16043* (2013.01)

(58) Field of Classification Search
CPC ........................... C12N 15/1138; C12N 15/86
See application file for complete search history.

(56) References Cited

U.S. PATENT DOCUMENTS

| | | | | |
|---|---|---|---|---|
| 5,928,638 A * | 7/1999 | Uchida | ................... | C12N 15/87 424/529 |
| 8,236,771 B2 * | 8/2012 | Cicciarelli | ........... | A61K 39/001 514/44 A |
| 9,677,087 B2 * | 6/2017 | Cicciarelli | ........... | A61K 39/001 |
| 2005/0106559 A1 * | 5/2005 | Radcliffe | ................ | C12N 15/86 435/5 |
| 2005/0227940 A1 * | 10/2005 | Rossi | ..................... | C12N 15/111 514/44 A |

* cited by examiner

*Primary Examiner* — Brian A Whiteman
(74) *Attorney, Agent, or Firm* — Brian J. Pangrle

(57) ABSTRACT

A kit for altering allogeneic human cells for a human recipient where the kit includes a set of lentivirus vectors where each of the lentivirus vectors expresses a sequence targeting a consensus conserved nucleic acid sequence, which when expressed in cells, functions as a negative modulator for nucleic acid encoding a domain having a mismatch in an HLA protein and where the set of lentivirus vectors includes individual lentivirus vectors that correspond to individual HLA mismatches for a set of HLA mismatches that consist of HLA Class I mismatches and at least one HLA Class II mismatch and where the kit is for treatment of human cells by an appropriate subset of the set of lentivirus vectors based at least in part on a determined subset of the set of HLA mismatches between a human donor and a human recipient or between human cells and a human recipient.

13 Claims, 14 Drawing Sheets
Specification includes a Sequence Listing.

FIG. 13

- GCCTTAGCTGTGCTCGCGCTACT (SEQ ID NO: 2)
- GAGGCTATCCAGCGTACTCCAAA (SEQ ID NO: 3)
- GTTTCATCCATCCGACATTGAAG (SEQ ID NO: 4)
- GTATGCCTGCCGTGTGAACCATG (SEQ ID NO: 5)
- GATAGTTAAGTGGGATCGAGACA (SEQ ID NO: 6)

Incorporation into hairpin siRNA constructs:

SEQUENCE LISTING

<160> NUMBER OF SEQ ID NOS: 38

<210> SEQ ID NO 1
<211> LENGTH: 23
<212> TYPE: DNA
<213> ORGANISM: Homo sapiens
<220> FEATURE:
<221> NAME/KEY: Human Beta 2-Microglobulin
<222> LOCATION: (1)..(23)

<400> SEQUENCE: 1
gagaatggaa agtcaaattt cct                                             23

<210> SEQ ID NO 2
<211> LENGTH: 23
<212> TYPE: DNA
<213> ORGANISM: Homo sapiens
<220> FEATURE:
<221> NAME/KEY: Human Beta 2-Microglobulin
<222> LOCATION: (1)..(23)

<400> SEQUENCE: 2
gccttagctg tgctcgcgct act                                             23

<210> SEQ ID NO 3
<211> LENGTH: 23
<212> TYPE: DNA
<213> ORGANISM: Homo sapiens
<220> FEATURE:
<221> NAME/KEY: Human Beta 2-Microglobulin
<222> LOCATION: (1)..(23)

<400> SEQUENCE: 3
gaggctatcc agcgtactcc aaa                                             23

<210> SEQ ID NO 4
<211> LENGTH: 23
<212> TYPE: DNA
<213> ORGANISM: Homo sapiens
<220> FEATURE:
<221> NAME/KEY: Human Beta 2-Microglobulin
<222> LOCATION: (1)..(23)

<400> SEQUENCE: 4
gtttcatcca tccgacattg aag                                             23

```
<210> SEQ ID NO 5
<211> LENGTH: 23
<212> TYPE: DNA
<213> ORGANISM: Homo sapiens
<220> FEATURE:
<221> NAME/KEY: Human Beta 2-Microglobulin
<222> LOCATION: (1)..(23)

<400> SEQUENCE: 5
gtatgcctgc cgtgtgaacc atg                                         23

<210> SEQ ID NO 6
<211> LENGTH: 23
<212> TYPE: DNA
<213> ORGANISM: Homo sapiens
<220> FEATURE:
<221> NAME/KEY: Human Beta 2-Microglobulin
<222> LOCATION: (1)..(23)

<400> SEQUENCE: 6
gatagttaag tgggatcgag aca                                         23

<210> SEQ ID NO 7
<211> LENGTH: 20
<212> TYPE: DNA
<213> ORGANISM: Homo sapiens
<220> FEATURE:
<221> NAME/KEY: A*020101 Allele of A Locus of Human MHC I
<222> LOCATION: (1)..(20)

<400> SEQUENCE: 7
ggattacatc gccctgaaag                                             20

<210> SEQ ID NO 8
<211> LENGTH: 20
<212> TYPE: DNA
<213> ORGANISM: Homo sapiens
<220> FEATURE:
<221> NAME/KEY: A*020101 Allele of A Locus of Human MHC I
<222> LOCATION: (1)..(20)

<400> SEQUENCE: 8
gcaggagggt ccggagtatt                                             20

<210> SEQ ID NO 9
<211> LENGTH: 20
<212> TYPE: DNA
<213> ORGANISM: Homo sapiens
<220> FEATURE:
<221> NAME/KEY: A*020101 Allele of A Locus of Human MHC I
<222> LOCATION: (1)..(20)

<400> SEQUENCE: 9
ggacggggag acacggaaag                                             20

<210> SEQ ID NO 10
<211> LENGTH: 19
<212> TYPE: DNA
<213> ORGANISM: Homo sapiens
<220> FEATURE:
<221> NAME/KEY: A*020101 Allele of A Locus of Human MHC I
<222> LOCATION: (1)..(19)

<400> SEQUENCE: 10
gaaagtgaag gcccactca                                              19
```

```
<210> SEQ ID NO 11
<211> LENGTH: 20
<212> TYPE: DNA
<213> ORGANISM: Homo sapiens
<220> FEATURE:
<221> NAME/KEY: A*020101 Allele of A Locus of Human MHC I
<222> LOCATION: (1)..(20)

<400> SEQUENCE: 11
gatacctgga gaacgggaag                                                   20

<210> SEQ ID NO 12
<211> LENGTH: 20
<212> TYPE: DNA
<213> ORGANISM: Homo sapiens
<220> FEATURE:
<221> NAME/KEY: A*020101 Allele of A Locus of Human MHC I
<222> LOCATION: (1)..(20)

<400> SEQUENCE: 12
gctgtggtgg tgccttctgg                                                   20

<210> SEQ ID NO 13
<211> LENGTH: 20
<212> TYPE: DNA
<213> ORGANISM: Homo sapiens
<220> FEATURE:
<221> NAME/KEY: A*020101 Allele of A Locus of Human MHC I
<222> LOCATION: (1)..(20)

<400> SEQUENCE: 13
gctactacaa ccagagcgag                                                   20

<210> SEQ ID NO 14
<211> LENGTH: 19
<212> TYPE: DNA
<213> ORGANISM: Homo sapiens
<220> FEATURE:
<221> NAME/KEY: A*020101 Allele of A Locus of Human MHC I
<222> LOCATION: (1)..(19)

<400> SEQUENCE: 14
gtggctccgc agatacctg                                                    19

<210> SEQ ID NO 15
<211> LENGTH: 9
<212> TYPE: DNA
<213> ORGANISM: Homo sapiens
<220> FEATURE:
<221> NAME/KEY: A*020101 Allele of A Locus of Human MHC I
<222> LOCATION: (1)..(9)

<400> SEQUENCE: 15 ttcaagaga                                                                9

<210> SEQ ID NO 16
<211> LENGTH: 11
<212> TYPE: DNA
<213> ORGANISM: Homo sapiens
<220> FEATURE:
<221> NAME/KEY: A*020101 Allele of A Locus of Human MHC I
<222> LOCATION: (1)..(11)

<400> SEQUENCE: 16
gtgtgctgtc c                                                            11
```

-continued

```
<210> SEQ ID NO 17
<211> LENGTH: 57
<212> TYPE: DNA
<213> ORGANISM: Homo sapiens
<220> FEATURE:
<221> NAME/KEY: A*020101 Allele of A Locus of Human MHC I
<222> LOCATION: (1)..(57)

<400> SEQUENCE: 17
tggattacat cgccctgaaa gtgtgctgtc ctttcagggc gatgtaatcc ttttttc       57

<210> SEQ ID NO 18
<211> LENGTH: 61
<212> TYPE: DNA
<213> ORGANISM: Homo sapiens
<220> FEATURE:
<221> NAME/KEY: A*020101 Allele of A Locus of Human MHC I
<222> LOCATION: (1)..(61)

<400> SEQUENCE: 18
tcgagaaaaa aggattacat cgccctgaaa ggacagcaca ctttcagggc gatgtaatcc    60
a                                                                   61

<210> SEQ ID NO 19
<211> LENGTH: 54
<212> TYPE: DNA
<213> ORGANISM: Homo sapiens
<220> FEATURE:
<221> NAME/KEY: A*020101 Allele of A Locus of Human MHC I
<222> LOCATION: (1)..(54)

<400> SEQUENCE: 19
tgcaggaggg tccggagtat tcaagagaat actccggacc ctcctgcttt tttc          54

<210> SEQ ID NO 20
<211> LENGTH: 58
<212> TYPE: DNA
<213> ORGANISM: Homo sapiens
<220> FEATURE:
<221> NAME/KEY: A*020101 Allele of A Locus of Human MHC I
<222> LOCATION: (1)..(58)

<400> SEQUENCE: 20
tcgagaaaaa agcaggaggg tccggagtat tctcttgaat actccggacc ctcctgca      58

<210> SEQ ID NO 21
<211> LENGTH: 57
<212> TYPE: DNA
<213> ORGANISM: Homo sapiens
<220> FEATURE:
<221> NAME/KEY: A*020101 Allele of A Locus of Human MHC I
<222> LOCATION: (1)..(57)

<400> SEQUENCE: 21
tggacgggga gacacggaaa gtgtgctgtc ctttccgtgt ctccccgtcc ttttttc       57

<210> SEQ ID NO 22
<211> LENGTH: 61
<212> TYPE: DNA
<213> ORGANISM: Homo sapiens
<220> FEATURE:
<221> NAME/KEY: A*020101 Allele of A Locus of Human MHC I
<222> LOCATION: (1)..(61)
```

<400> SEQUENCE: 22
tcgagaaaaa aggacgggga gacacggaaa ggacagcaca ctttccgtgt ctccccgtcc    60
a    61

<210> SEQ ID NO 23
<211> LENGTH: 54
<212> TYPE: DNA
<213> ORGANISM: Homo sapiens
<220> FEATURE:
<221> NAME/KEY: A*020101 Allele of A Locus of Human MHC I
<222> LOCATION: (1)..(54)

<400> SEQUENCE: 23
tgaaagtgaa ggcccactca ttcaagagat gagtgggcct tcactttctt tttc    54

<210> SEQ ID NO 24
<211> LENGTH: 58
<212> TYPE: DNA
<213> ORGANISM: Homo sapiens
<220> FEATURE:
<221> NAME/KEY: A*020101 Allele of A Locus of Human MHC I
<222> LOCATION: (1)..(58)

<400> SEQUENCE: 24
tcgagaaaaa gaaagtgaag gcccactcat ctcttgaatg agtgggcctt cactttca    58

<210> SEQ ID NO 25
<211> LENGTH: 56
<212> TYPE: DNA
<213> ORGANISM: Homo sapiens
<220> FEATURE:
<221> NAME/KEY: A*020101 Allele of A Locus of Human MHC I
<222> LOCATION: (1)..(56)

<400> SEQUENCE: 25
tgatacctgg agaacgggaa gtgtgctgtc cttcccgttc tccaggtatc tttttc    56

<210> SEQ ID NO 26
<211> LENGTH: 60
<212> TYPE: DNA
<213> ORGANISM: Homo sapiens
<220> FEATURE:
<221> NAME/KEY: A*020101 Allele of A Locus of Human MHC I
<222> LOCATION: (1)..(60)

<400> SEQUENCE: 26
tcgagaaaaa gatacctgga gaacgggaag gacagcacac ttcccgttct ccaggtatca    60

<210> SEQ ID NO 27
<211> LENGTH: 57
<212> TYPE: DNA
<213> ORGANISM: Homo sapiens
<220> FEATURE:
<221> NAME/KEY: A*020101 Allele of A Locus of Human MHC I
<222> LOCATION: (1)..(57)

<400> SEQUENCE: 27
tgctgtggtg gtgccttctg gtgtgctgtc ccagaaggca ccaccacagc tttttc    57

<210> SEQ ID NO 28
<211> LENGTH: 61
<212> TYPE: DNA
<213> ORGANISM: Homo sapiens
<220> FEATURE:
<221> NAME/KEY: A*020101 Allele of A Locus of Human MHC I
<222> LOCATION: (1)..(61)

<400> SEQUENCE: 28
tcgagaaaaa agctgtggtg gtgccttctg ggacagcaca ccagaaggca ccaccacagc    60
a                                                                    61

<210> SEQ ID NO 29
<211> LENGTH: 57
<212> TYPE: DNA
<213> ORGANISM: Homo sapiens
<220> FEATURE:
<221> NAME/KEY: A*020101 Allele of A Locus of Human MHC I
<222> LOCATION: (1)..(57)

<400> SEQUENCE: 29
tgctactaca accagagcga gtgtgctgtc ctcgctctgg ttgtagtagc tttttc        57

<210> SEQ ID NO 30
<211> LENGTH: 61
<212> TYPE: DNA
<213> ORGANISM: Homo sapiens
<220> FEATURE:
<221> NAME/KEY: A*020101 Allele of A Locus of Human MHC I
<222> LOCATION: (1)..(61)

<400> SEQUENCE: 30
tcgagaaaaa agctactaca accagagcga ggacagcaca ctcgctctgg ttgtagtagc    60
a                                                                    61

<210> SEQ ID NO 31
<211> LENGTH: 57
<212> TYPE: DNA
<213> ORGANISM: Homo sapiens
<220> FEATURE:
<221> NAME/KEY: A*020101 Allele of A Locus of Human MHC I
<222> LOCATION: (1)..(57)

<400> SEQUENCE: 31
tgtggctccg cagatacctg gtgtgctgtc ccaggtatct gcggagccac tttttc        57

<210> SEQ ID NO 32
<211> LENGTH: 61
<212> TYPE: DNA
<213> ORGANISM: Homo sapiens
<220> FEATURE:
<221> NAME/KEY: A*020101 Allele of A Locus of Human MHC I
<222> LOCATION: (1)..(61)

<400> SEQUENCE: 32
tcgagaaaaa agtggctccg cagatacctg ggacagcaca ccaggtatct gcggagccac    60
a                                                                    61

<210> SEQ ID NO 33
<211> LENGTH: 1098
<212> TYPE: DNA
<213> ORGANISM: Homo sapiens
<220> FEATURE:
<221> NAME/KEY: A*020101 Allele of Human Class I MHC
<222> LOCATION: (1)..(1098)

<400> SEQUENCE: 33
atggccgtca tggcgccccg aaccctcgtc ctgctactct cgggggctct ggccctgacc    60
cagacctggg cgggctctca ctccatgagg tatttcttca catccgtgtc ccggcccggc   120
cgcggggagc ccgcttcat cgcagtgggc tacgtggacg acacgcagtt cgtgcggttc   180

| | |
|---|---|
| gacagcgacg ccgcgagcca gaggatggag ccgcgggcgc cgtggataga gcaggagggt | 240 |
| ccggagtatt gggacgggga gacacggaaa gtgaaggccc actcacagac tcaccgagtg | 300 |
| gacctgggga ccctgcgcgg ctactacaac cagagcgagg ccggttctca caccgtccag | 360 |
| aggatgtatg gctgcgacgt ggggtcggac tggcgcttcc tccgcgggta ccaccagtac | 420 |
| gcctacgacg gcaaggatta catcgccctg aaagaggacc tgcgctcttg gaccgcggcg | 480 |
| gacatggcag ctcagaccac caagcacaag tgggaggcgg cccatgtggc ggagcagttg | 540 |
| agagcctacc tggagggcac gtgcgtggag tggctccgca gatacctgga gaacgggaag | 600 |
| gagacgctgc agcgcacgga cgcccccaaa acgcatatga ctcaccacgc tgtctctgac | 660 |
| catgaagcca ccctgaggtg ctgggccctg agcttctacc ctgcggagat cacactgacc | 720 |
| tggcagcggg atggggagga ccagacccag gacacggagc tcgtggagac caggcctgca | 780 |
| gggatggaa ccttccagaa gtgggcggct gtggtggtgc cttctggaca ggagcagaga | 840 |
| tacacctgcc atgtgcagca tgagggtttg cccaagcccc tcaccctgag atgggagccg | 900 |
| tcttcccagc ccaccatccc catcgtgggc atcattgctg gcctggttct ctttggagct | 960 |
| gtgatcactg gagctgtggt cgctgctgtg atgtggagga ggaagagctc agatagaaaa | 1020 |
| ggagggagct actctcaggc tgcaagcagt gacagtgccc agggctctga tgtgtctctc | 1080 |
| acagcttgta aagtgtga | 1098 |

<210> SEQ ID NO 34
<211> LENGTH: 1098
<212> TYPE: DNA
<213> ORGANISM: Homo sapiens
<220> FEATURE:
<221> NAME/KEY: B*070201 Allele of Human Class I MHC
<222> LOCATION: (1)..(1098)

<400> SEQUENCE: 34

| | |
|---|---|
| atgctggtca tggcgccccg aaccgtcctc ctgctgctct cggcggccct ggccctgacc | 60 |
| gagacctggg ccggctccca ctccatgagg tatttctaca cctccgtgtc ccggcccggc | 120 |
| cgcggggagc cccgcttcat ctcagtgggc tacgtggacg acacccagtt cgtgaggttc | 180 |
| gacagcgacg ccgcgagtcc gagagaggag ccgcgggcgc cgtggataga gcaggagggg | 240 |
| ccggagtatt gggaccggaa cacacagatc tacaaggccc aggcacagac tgaccgagag | 300 |
| agcctgcgga acctgcgcgg ctactacaac cagagcgagg ccgggtctca caccctccag | 360 |
| agcatgtacg gctgcgacgt ggggccggac gggcgcctcc tccgcgggca tgaccagtac | 420 |
| gcctacgacg gcaaggatta catcgccctg aacgaggacc tgcgctcctg gaccgccgcg | 480 |
| gacacggcgg ctcagatcac ccagcgcaag tgggaggcgg ccgtgaggc ggagcagcgg | 540 |
| agagcctacc tggagggcga gtgcgtggag tggctccgca gatacctgga gaacgggaag | 600 |
| gacaagctgg agcgcgctga ccccccaaag acacacgtga cccaccaccc catctctgac | 660 |
| catgaggcca ccctgaggtg ctgggccctg ggtttctacc ctgcggagat cacactgacc | 720 |
| tggcagcggg atggcgagga ccaaactcag gacactgagc ttgtggagac cagaccagca | 780 |
| ggagatagaa ccttccagaa gtgggcagct gtggtggtgc cttctggaga agagcagaga | 840 |
| tacacatgcc atgtacagca tgagggctg ccgaagcccc tcaccctgag atgggagccg | 900 |
| tcttcccagt ccaccgtccc catcgtgggc attgttgctg gcctggctgt cctagcagtt | 960 |
| gtggtcatcg gagctgtggt cgctgctgtg atgtgtagga ggaagagttc aggtggaaaa | 1020 |

```
ggagggagct actctcaggc tgcgtgcagc gacagtgccc agggctctga tgtgtctctc    1080
acagcttgaa aagcctga                                                   1098

<210> SEQ ID NO 35
<211> LENGTH: 1101
<212> TYPE: DNA
<213> ORGANISM: Homo sapiens
<220> FEATURE:
<221> NAME/KEY: Cw*070101 Allele of Human Class I MHC
<222> LOCATION: (1)..(1101)

<400> SEQUENCE: 35
atgcgggtca tggcgccccg agccctcctc ctgctgctct cgggaggcct ggccctgacc      60
gagacctggg cctgctccca ctccatgagg tatttcgaca ccgccgtgtc ccggcccggc     120
cgcggagagc cccgcttcat ctcagtgggc tacgtggacg acacgcagtt cgtgcggttc     180
gacagcgacg ccgcgagtcc gagaggggag ccgcgggcgc cgtgggtgga gcaggagggg     240
ccggagtatt gggaccggga gacacagaac tacaagcgcc aggcacaggc tgaccgagtg     300
agcctgcgga acctgcgcgg ctactacaac cagagcgagg acgggtctca caccctccag     360
aggatgtatg gctgcgacct ggggcccgac gggcgcctcc tccgcgggta tgaccagtcc     420
gcctacgacg gcaaggatta catcgccctg aacgaggacc tgcgctcctg gaccgccgcg     480
gacaccgcgg tcagatcac ccagcgcaag ttggaggcgg cccgtgcggc ggagcagctg     540
agagcctacc tggagggcac gtgcgtggag tggctccgca gatacctgga gaacgggaag     600
gagacgctgc agcgcgcaga accccaaag acacacgtga cccaccaccc cctctctgac     660
catgaggcca ccctgaggtg ctgggccctg gcttctacc ctgcggagat cacactgacc     720
tggcagcggg atggggagga ccagacccag gacaccgagc ttgtggagac caggccagca     780
ggagatggaa ccttccagaa gtgggcagct gtggtggtgc cttctggaca agagcagaga     840
tacacgtgcc atatgcagca cgaggggctg caagagcccc tcaccctgag ctgggagcca     900
tcttcccagc ccaccatccc catcatgggc atcgttgctg gcctggctgt cctggttgtc     960
ctagctgtcc ttggagctgt ggtcaccgct atgatgtgta ggaggaagag ctcaggtgga    1020
aaaggaggga gctgctctca ggctgcgtgc agcaacagtg cccagggctc tgatgagtct    1080
ctcatcactt gtaaagcctg a                                              1101

<210> SEQ ID NO 36
<211> LENGTH: 16
<212> TYPE: DNA
<213> ORGANISM: Homo sapiens
<220> FEATURE:
<221> NAME/KEY: Microtubule-Associated Protein 6 mRNA
<222> LOCATION: (1)..(16)

<400> SEQUENCE: 36
aatggaaagt caaatt                                                      16

<210> SEQ ID NO 37
<211> LENGTH: 16
<212> TYPE: DNA
<213> ORGANISM: Homo sapiens
<220> FEATURE:
<221> NAME/KEY: MyelinGeneExpressionFactor2mRNA
<222> LOCATION: (1)..(16)
<220> FEATURE:
<221> NAME/KEY: Myelin Gene Expression Factor 2 mRNA
<222> LOCATION: (1)..(16)
```

```
<400> SEQUENCE: 37
agaatggaaa gtcaaa                                                  16

<210> SEQ ID NO 38
<211> LENGTH: 17
<212> TYPE: DNA
<213> ORGANISM: Homo sapiens
<220> FEATURE:
<221> NAME/KEY: Prokineticin 2 mRNA
<222> LOCATION: (1)..(17)

<400> SEQUENCE: 38
gaatggaaag ccaaatt                                                 17
```

VECTORS AND METHODS FOR LONG-TERM IMMUNE EVASION TO PROLONG TRANSPLANT VIABILITY

RELATED APPLICATION

This application is a continuation of U.S. nonprovisional application Ser. No. 13/567,064 filed Aug. 5, 2012 (issued as U.S. Pat. No. 9,677,087 on Jun. 13, 2017), which is hereby incorporated herein in its entirety, which is a continuation of U.S. nonprovisional application Ser. No. 11/131,507 filed May 18, 2005 (issued as U.S. Pat. No. 8,236,771 on Aug. 7, 2012), which is hereby incorporated herein in its entirety and which claims the benefit of U.S. provisional application Ser. No. 60/571,873 filed May 18, 2004, which is hereby incorporated herein in its entirety.

REFERENCE TO SEQUENCE LISTING AND TABLES

A Sequence Listing, as submitted electronically (as a text file processed via PatentIn v. 3.3) with U.S. nonprovisional application Ser. No. 11/131,507 filed May 18, 2005, is incorporated by reference herein. An Appendix with Tables 1 and 3, as submitted with U.S. nonprovisional application Ser. No. 11/131,507 filed May 18, 2005, appears at the end of this specification.

TECHNICAL FIELD

This invention relates to the field of cell and organ transplantation, and describes a general method to achieve long-term suppression of cellular proteins that elicit or potentiate host immune responses against un-matched donor antigens.

BACKGROUND

Immune responses against donor (i.e., "non-self" or "allogeneic") antigens are the primary cause of rejection of the transplanted cells, resulting in graft failure. To date, the primary strategies for avoiding rejection have been to minimize antigenic differences between donor and recipient by matching Human Leukocyte Antigens (HLA; also known as Major Histocompatibility (MHC) antigens) and by subjecting the transplant recipient to potent immunosuppression.

HLA antigens are encoded by several gene loci; of these, the most important for graft survival are the HLA Class I antigens A and B (see FIG. 1), and the Class II antigen (FIG. 2) DR. An HLA matching effect was significantly associated with HLA-A, B, and DR match in kidney transplantation and has an overall significant effect for graft survival and/or rejection in pancreas, heart, lung and bone marrow transplantation. In liver transplants, matching was associated with less rejection but was also associated with reoccurrence of disease. Thus, the extent to which the HLA-A, B, and DR loci antigens are matched is currently one of the most significant parameters affecting outcome in most solid organ and bone marrow transplants.

Kidney Transplants

Many factors are associated with increased renal transplant survival, one of which is living-related donors, who will generally have more closely matched set of HLA antigens than unrelated donors. Patients cannot always benefit from a living-related transplant compared to a cadaveric renal transplant if risk factors were increased in a living donor transplant [7]. For example, graft survival in recipients 18 to 59 years of age with a live 50-year-old kidney donor is comparable or decreased compared with a cadaveric renal transplant if the cadaveric donor is much younger or has fewer HLA mismatches. On the other hand, cadaver renal transplants in recipients over 60 never provide better outcome than living-related transplants. These are significant observations since live donor transplantation now comprises more than 40% of all kidney transplantation and will continue to be a large part of renal transplantation [8] as long as the number of cadaver donors remains constant, as it has through the last ten years. In either case, mismatching of HLA antigens incurs immune responses that reduce graft survival.

It has been shown that race is one of the risk factors associated with renal transplant results. Asians have very high graft survival rates and the question has been raised regarding whether or not matching has an effect on results. However, Opelz [9] shows that HLA matching does have an additive effect on graft survival in Asians.

HLA-DP allele matching in renal transplants was known to have a significant effect on renal graft survival. Examination of regraft recipients which were all one allele match, showed that immunogenetic epitopes were important to match [10]. These results corroborate the importance of immunogenicity, noting that alleles may not always be immunogenic. This is quite similar to the result found in bone marrow transplantation with "alleles" solely defined by molecular techniques [47, 48, 49].

There has been an ongoing contention that new immunosuppressive drugs improve graft survival rates, which proscribes the need for HLA matching [1, 2, 3]. In an analysis [1] with over 52,000 transplants from 1978 through 2000, the transplants were broken into three eras: the first was—1978 to 1984, prior to calcinurin inhibitor drugs cyclosporin A (CsA) and FK-506; the CsA era, 1987 through 1994; and after extensive use of FK-506 from 1995 to 2000. Results were shown with each match grade and 10-year graft survival. In every instance, notwithstanding the difference in immunosuppressive drugs utilized, the 10-year graft survival difference between zero mismatch and six antigens mismatch was 18%.

This consistent difference was found even though transplantation has changed dramatically through the years. That is, one year graft survivals were 58% in 1978-84 as compared to 86% in the most recent (1995 to 2000) era. In addition to major changes in immunosuppression, there has been a policy for prospective matching of zero HLA-A, B, DR donor mismatched patients in the USA. In the '78-'84 era, the number of zero mismatched patients was two-hundred eleven (2%) and in the most recent era, 1995 to 2000, 6,279 (14%) HLA zero mismatched patients were transplanted. From the large difference between zero and one mismatch, it is clear that even one antigen mismatch was enough for the immune system to respond and react vigorously. Also, there was an additive increase in graft survival for each mismatched antigen, with the largest increase occurring from one to zero.

Renal transplant half-life data shows an advantage to HLA matching at all match grades, particularly at zero mismatch. Half-life increases as match increases and also increases with better immunosuppression. Furthermore, both the matching and immunosuppressive effects are additive. New changes in kidney allocation by United Network for Organ Sharing (UNOS) eliminate HLA-B, DR matching points in an attempt to decrease the disadvantage to minorities and those with rare HLA types. Because of the contribution of each HLA A, B, DR match, this algorithm change will reduce graft survival in transplant recipients.

Pancreas Transplants

Overall, graft survival in pancreas transplants is lower than in kidney transplants. One possibility for these discrepant outcomes as compared to kidneys, results from diabetic complications. Functional pancreas graft survival, excluding patients that die with a functioning graft, compared to functional kidney graft survival gives similar results, presumably because there is a higher death rate due to diabetic complications.

The role of HLA matching in pancreas transplantation is somewhat controversial. Two recent investigations have reported little HLA matching effect since one year and 5-year graft survival of matched and non-matched were similar [12, 13]; however, the number of transplants examined was quite small. In fact, it has been shown in the international pancreas registry [11] that pancreas after kidney, or pancreas transplant alone, has an HLA Class I matching effect such that if one antigen is matched at either HLA-A or B loci, there are significant one-year pancreas survival rates of 85% and 74% respectively, versus 70% and 60% for the non-matched. Furthermore, poorly matched patients have shown significant increases in rejection [14].

In pancreas transplant recipients, autoantibody to each of islet cells and glutamic acid carboxylase was found in patients with graft complications [15]. Furthermore, pancreas transplant recipients with rejection have anti-HLA Class I and Class II antibodies developing post-transplant [16]. HLA Class II antibodies were significantly associated with risk of chronic allograft rejection [16].

Liver Transplantation

Although the influence of matching on outcome of liver graft survival is controversial [17, 18], HLA-A and B matching is significantly associated with lower graft rejection [18, 19], but there was no beneficial effect of matching HLA-DR. Furthermore, if HLA-DR was matched in liver transplant patients, certain disease conditions increase or may recur; therefore, HLA DR played a role in the etiology of the disease [20].

In hepatitis-B infected liver transplant recipients, there was significant graft survival improvement in patients with HLA-A and B compatibilities but not DR [21]. Specificities of HLA Class II antigens were associated with reduced risk for viral infections, that is HLA-DR 11 and HLA-DQ-3 antigen occurrence in the recipient candidates is a reduced risk for hepatitis C infection [22]. Also, the frequency of HLA-DQ-0302 (an allele of DQ-3) was significantly higher in liver graft recipients with acute rejection [23]. Preformed HLA antibodies have not been associated with graft rejection problems such that positive crossmatch is not necessarily a contra-indication for liver transplantation. This is partly due to the liver's large organ mass, its consequent ability to absorb or "sponge up" the antibodies without any deleterious consequences. In small size grafts with positive flow crossmatches, rejection episodes and organ failure have been noted in four cases [24].

Heart Transplantation

Heart transplant outcomes show a significant correlation to HLA matching [25-28]. In zero mismatches, there is a decrease in risk ratio as the number of matches increases. In one study [28] there seems to be an association between the different HLA loci matches and the risk ratio. That is, HLA-A locus matching may be potentiating antigen presentation in heart recipients, such that there was lower graft survival in HLA-A locus matched transplants. Recent studies [25, 26] have shown similar results. Again, because there is no prospective heart transplant matching system in place, large numbers of well-matched transplants are not available for analysis.

Using left ventricular assist devices has been an important advance as a bridge to cardiac transplantation. However, sensitization to HLA antigens occurs in patients using the left ventricular system devices [29, 30]. In these sensitized patients there was increased acute rejection, but not a decrease in graft survival [29, 30], when compared to non-sensitized patients. A major finding with left ventricular assist devices has been that even though antibody is produced, it can be controlled through plasmapheresis and also through treatment with IVIG and/or Retuxin, an anti CD20 antibody. In other studies, HLA antibodies were associated with a significantly higher incidence of graft rejection episodes and graft loss in heart transplant recipients [31, 32]. This may be reconciled with the above studies [29, 30] in that antibodies are demonstrated by two methods—complement dependent and flow cytometry panel reactive antibodies. The latter shows a much higher correlation to graft loss and rejection, whereas the former shows less correlation because of the relative insensitivity of the test.

HLA-G is an HLA Class I antigen associated with the trophoblast, which inhibits cellular immunity during pregnancy. In cardiac transplants expressing HLA-G, acute rejection was significantly lower [33], and chronic rejection was not found. IL-2 lymphokine polymorphisms may also show an important significant correlation with outcomes [34]. Furthermore, there was a complex interaction with HLA-DR matching, such that patients with IL-2 polymorphisms significantly associated with acute rejection had a better outcome if they were HLA-DR matched.

Lung Transplantation

In lung transplantation, Bronchiolitis Obliterans Syndrome (BOS) is a manifestation of the rejection and graft loss process. The test for BOS is based on forced air volume declining to less than 80% of baseline as well as fibrosis and death of airway epithelial cells. An association was observed between the HLA matching and BOS [35, 36, 37, 38, 39], with different effects noted for HLA Class I and Class II [35, 36, 37, 38]; that is, there was a trend of poorly matched HLA-DR and HLA-A recipients having a significant risk for BOS. Upon examination of the total number of HLA-A, B, and DR mismatches [36], there is a significant association was observed with the appearance of BOS, but not with 5-year mortality rates, which seemed to correlate with repeat regrafting, congenital heart disease, and recipient age. Again, HLA-DR is associated with the appearance of BOS and also graft loss [37, 38]. One long-term study showed significant association of HLA-A and B mismatches, with the occurrence of BOS [39]. In this long-term study, the HLA-A, B mismatches were strongly associated (P=0.002) with the occurrence of BOS at 4 years, and none of the other factors, such as donor/recipient age, ischemia time, pulmonary bypass, episodes of acute rejection, CMV, pneumonitis, or CsA trough levels, had any long-term consequences associated with the occurrence of BOS or graft survival [39]. Matching trends were uncertain since there were not a large number of well-matched patients in these lung transplant studies.

With regard to the BOS post-transplant and an association with HLA antibodies, several papers [40, 41, 42, 43, 44] show the correlation of HLA antibody with the occurrence of BOS. Furthermore, monoclonal antibodies to HLA common antigens stimulated in vitro airway epithelial cell proliferation, which is an initiation event in the development of BOS [40]. Patients who have post-transplant antibody, 90% of which is developed against HLA Class II antigens, showed a significant (P=0.005) association for the development of BOS [41]. Furthermore, in a small study, BOS and death was reported during the follow-up period in four patients who had pre-formed anti-HLA antibodies. Albeit, this was a small study, Class II antibody specificities may have played an important role in both the development of BOS and the chronic rejection. It is an object of an embodiment of the invention herein to avoid sensitization prior to transplant because of the occurrence of BOS and the ultimate death of these recipients.

The mechanism by which the development of BOS occurs with HLA antibody is only partially understood [43, 44]. Antibodies can initiate the cascade of proliferation and formation of growth factor leading to fibrosis. Furthermore, apoptosis is also associated with an anti-HLA antibody binding to the airway epithelial cells [44].

A clear T-cell immune response to HLA Class I and Class II antigens was associated with patients who have BOS [45]. Lymphokine polymorphisms in BOS patients showed significant correlation to high producing IL-6 and interferon gamma, the latter cause de novo synthesis HLA Class II antigens and, therefore, are linked to the association between HLA Class II antibody and the appearance of BOS [46].

Bone Marrow Transplantation

Bone marrow transplantation is distinguished from solid organ transplants since the organ being transplanted is the hematopoietic and immune system. Therefore, in recipients, the host bone marrow is ablated or killed so that it does not react to the donor bone marrow. Furthermore, if there is any recipient HLA antigen mismatching to the donor, graft vs host disease can occur which can have severe complications [47]. Therefore recipient mismatches are relevant whereas in solid organ transplants one is concerned with the donor mismatches. For these reasons, HLA perfectly matched bone marrow transplantation is desirable. Small molecular genetic differences are found to cause bone marrow transplant rejection [48]. These HLA differences can basically be divided into those serologically defined and those that are molecularly defined. In the former case, there may be more than one molecularly based epitope difference in the molecule, whereas, in the latter, a clearly defined single sequence difference is associated with the molecular antigen. It has recently been shown that if one mismatches the serological antigens, this is enough to increase the probability of graft failure [49], however, a single HLA molecular mismatched antigen does not result in increased graft failure. Since HLA is remarkably polymorphic with more than 220, 460, 110, and 360 molecularly defined epitopes for HLA-A, B, C, and DR respectively, the manner in which antigens are defined, and which antigens are mismatched plays an important role in future bone marrow transplantations and in finding a match.

Treatment protocols and bone marrow graft survivals are quite different, depending on the disease of patients being transplanted. Results vary depending upon leukemia type, solid tumor, or syndrome that is treated [50, 51].

Matching HLA-C locus (a generally weakly expressed Class I antigen) may be important regarding the activation of natural killer cells, since C locus serves as a killing receptor inhibitor [52]. It has been shown that one mismatch at the C locus, i.e. the absence of one killing receptor inhibitor, is enough to activate an allogeneic NK cell killing.

As in solid organ transplants above, the association of genetic polymorphism of interferon gamma and IL6 high producing phenotypes has recently been associated with graft vs host disease [53].

Cornea Grafts

Cornea grafts have not been associated with the HLA matching effect [54]. Recently, however, this has been challenged [55, 56] by results showing HLA matching especially HLA-DR, to be significantly correlated to outcome. HLA antibodies have been a significant problem in corneal grafts when observed, and are correlated with poor outcomes [54].

Immune Reactivity to HLA

An in-vitro correlate, i.e. assay, for humoral and cellular response is the formation of HLA specific antibody. That is, with the IgG immunoglobulin formation, there is the requirement of CD4 T cell activation with concomitant Class II antigen presentation. Therefore, the presence of IgG (as demonstrated with panel reactive antibodies) implicates CD4 T-cells and B-cells directly. It is envisioned herein that rejection and/or graft loss as a consequence of the immune response to HLA antigens would usually, if not always, show HLA antibody as an in vitro correlate.

However, until recently, an association of HLA antibody and transplant rejection and loss was not clear. With the advent of new, more sensitive IgG specific techniques such as flow PRA [57] and ELISA [58] in renal transplants [59], it has recently been shown that 96% of all patients who had rejected kidneys had HLA antibody present post-rejection [60]. It has been long known that preformed donor specific HLA antibodies in kidney transplant recipients can be utilized to determine the risk of hyperacute rejection [60-62].

HLA antibodies in renal transplants are associated with acute rejection [64-66]. Furthermore, there seems to be an association between HLA antibody, specifically Class II antibody [16, 41, 66] and chronic rejection, as recently reviewed [67].

SUMMARY OF THE EMBODIMENTS

An embodiment of the invention provides a virus vector comprising a nucleic acid sequence encoding a negative modulator of a polymorphic target having conserved domains, and the target is an immune recognition/activation protein. The term "polymorphic" with respect to the target protein means that the protein has variants in amino acid sequence within a population, and because of the presence of alleles on the two homologous chromosomes of an individual, may even be polymorphic within an individual subject. Within the amino acid sequences of different variants of a polymorphic protein can be found the conserved domains.

In an alternative embodiment, the invention provides a virus vector comprising a nucleic acid sequence which contains a sequence that, when expressed, functions as a negative modulator of a non-polymorphic target having conserved domains, and the target is an immune recognition/activation protein, i.e., the target protein need not be polymorphic.

In general, the modulator is an RNA transcript produced from the vector. For example, the RNA is a small interfering RNA (siRNA) or an antisense RNA. The target protein includes a domain of subunit of protein selected from the group of an MHC class I, MHC class II, a co-stimulatory molecule, and an immuno-modulatory signaling receptor. In general, an immunomodulatory receptor has an activating function for the immune system, for example, by signal transmission among cells of the immune system, however following use of the viral vectors provided herein, the expression of this protein is inhibited. For example, the MHC class I subunit is selected from α1, α2, α3 and β2-microglobulin (β2-MG) as shown in FIG. 1. Further in one embodiment, the MHC class I α3 domain is a loop that interacts with CD8. Alternatively, the MHC class II subunit is selected from α1, β1, and β2 as shown in FIG. 2. Further, the β2 domain is a loop that interacts with CD4.

In certain embodiments, the nucleotide sequence of the modulator is selected from SEQ ID NOs: 1-32. For example, the nucleotide sequence targeting the human MHC I α domains are selected from SEQ ID NOs: 7-14. Sequences specific to the β2-microglobulin subunit of human MHC I can be chosen for targeting with siRNA or antisense, and such sequences as identified here as SEQ ID NOs: 1-6. Sequences specific to the A locus of human MHC I can be chosen for targeting with siRNA or antisense, and such sequences as identified here as SEQ ID NOs: 7-10. Sequences common among the A, B and C loci of human MHC I can be chosen for targeting with siRNA or antisense, and such sequences as identified here as SEQ ID NOs: 11-14. Sequences are inserted into a 9-bp loop, SEQ ID NO:15, or an 11-bp loop, SEQ ID NO:16, generating nucleic acid sequences of oligonucleotides specific to the A locus of human MHC I, exemplified herein as SEQ ID NOs: 17-24 (as pairs of forward and reverse oligonucleotides). Similarly, sequences are inserted into a 9-bp loop, SEQ ID NO:15, or an 11-bp loop, SEQ ID NO:16, generating nucleic acid sequences of oligonucleotides common to the A, B and C loci of human MHC I, exemplified herein as SEQ ID NOs: 25-32 (as pairs of forward and reverse oligonucleotides). Locations of sequences within the amino acid sequences of class I MHC proteins can be found using the following alleles: A*020101, B*070201, and Cw*070101, provided herein as SEQ ID NOs: 32-34, respectively.

In certain embodiments, the vector is selected from the group consisting of: a lentivirus, an adeno-associated virus, and a helper-dependent adenovirus. The lentivirus can be a strain or a derivative of a human immunodeficiency virus (HIV), a simian immunodeficiency virus (SIV), a feline immunodeficiency virus (FIV) or an equine infectious anemia virus (EIAV). Without being limited to any particular examples, the lentivirus is in various exemplary embodiments derived from a commercially available virus vector preparation that is produced by co-transfection of the lentiviral packaging plasmid pCMVΔR 8.91, the VSV-G envelope plasmid pMD.G, and the lentiviral vector construct plasmid pRRLsin-CMV-GFP, or a functional equivalent thereof.

In alternative embodiments, the co-stimulatory molecule is CD80 (B7.1) or CD86 (B7.2). Alternatively the co-stimulatory molecule is a potentiating inflammatory cytokine or its cognate receptor. Inflammatory proteins such as these function to stimulate the immune response, and consequently adversely affect the life-time of a tissue, organ or cell graft. Exemplary potentiating inflammatory cytokines are γ-interferon, IL-1, IL-2, TNFα, TGFβ, or a receptor for any of these proteins.

In another embodiment the invention provides a method of making a virus vector comprising a nucleic acid sequence encoding a negative modulator of a conserved immunoregulatory target, the method comprising: identifying a target domain of an immunopotentiating protein, wherein the immunopotentiating protein is selected from an MHC molecule, an inflammatory cytokine or a receptor therefor; locating a suitable nucleotide sequence of an encoding RNA for silencing by siRNA or antisense RNA; and constructing an siRNA or antisense expression cassette and inserting it into a recombinantly engineered nucleic acid of the vector.

In a related embodiment the method involves contacting donor cells and thereby transducing the cells with the vector. The term "transducing" is used to indicate that a viral infection results in transmission of genetic material that alters the genome of the recipient cells, providing genetic information to these cells that remains for a period of time longer than a mere transient transfection. In a related embodiment the method further involves transferring the transduced cells to a mammalian subject. Alternatively, locating the sequence further comprises searching a computer database of a genome.

In yet another embodiment the invention provides a method of preparing a tissue, cell or organ graft for a subject recipient, the method comprising: identifying at least one mismatch in HLA proteins; and contacting the donor cells with a virus vector that expresses a negative modulator of an immune recognition or activation protein for the at least one mismatched HLA. The mismatch can be endogenous within the donor cells, i.e., that the two alleles carried on homologous chromosomes are different variants of the protein, or the mismatch can be between donor cells and the recipient subject, or both mismatches may be observed.

In a related embodiment, the donor graft is a hematopoietic cell such as a hematopoietic stem cell, a hemangioblast cell, or is a tissue which is a bone marrow, a mismatch in the recipient or between donor and recipient is further treated by contacting recipient cells with a virus vector that expresses a negative modulator of an immune recognition or activation protein for the at least one mismatched HLA.

In a related embodiment the method further includes administering the contacted cells to the recipient, thereby decreasing donor cell immunogenicity and increasing graft half-life in the recipient. In the alternative embodiment following administration to recipient contacted cells, the method further involves observing a decrease in graft-versus-host disease. In a related embodiment, the method further involves following administering, observing the graft of contacted donor cells having a greater lifetime in the subject than a donor cell that is otherwise identical but not similarly contacted. In a related embodiment, the subject is in need of a transplant having cells or a tissue of an organ.

In general, the donor tissue or cell population for the methods herein is selected from the group of: kidney, pancreas, liver, heart, lung, stem cells, bone marrow, fetal cord blood, peripheral blood mononuclear cells, T lymphocytes, and cornea. The stem cells may be from a pure cell culture, i.e., cultured in vitro, or may enriched or purified from other tissues, such as fetal cord blood. The stem cells include, without limitation: hematopoietic stem cells, mesenchymal stem cells, and hemangioblast cells. Stem cells may include cells that are at a mixture of different phases in development of a mature cell, or may be uniform in stage of development. In general, the subject recipient is in need of a transplant of cells derived from an organ that is selected from a kidney; pancreas; liver; heart; lung; brain; bone marrow; and cornea.

The invention having now been fully described it is further exemplified by the following examples and claims which are exemplary and are not intended to be further limiting. The contents of all papers cited herein are hereby incorporated herein in their entireties.

BRIEF DESCRIPTIONS OF THE DRAWINGS

FIG. 1 is a drawing of an MHC class I protein showing the subunits and domains, and relationships to the cell membrane. The α heavy chain has three domains, and the majority of antigenic determinants are in α1 and α2. The α3 domain and β2-microglobulin (β2-MG) subunit each have one 13 pleated sheet which associate with each other non-covalently. The α1 and α2 domains have 4-strand β sheets and 1α helix. The two α helices form the binding cleft and the β sheets form the floor of the cleft. The α3 domain has a non-polymorphic loop which interacts with CD8, and the β2-MG subunit is invariant.

FIG. 2 is a drawing of an MHC class II protein consisting of two chains, α and β, each having two domains. The α1 and β1 domains have 4-stranded β sheets which form the floor of the cleft made up of two α helices. The β2 domain has a non-polymorphic loop which interacts with CD4.

FIG. 3 is a drawing showing generation of U6 transcription cassettes expressing siRNAs, by polymerase chain reaction (PCR).

FIG. 4 is a drawing of a map of plasmid pLentiLox-Red having 7638 base pairs showing restriction enzyme digestion sites on the outside and functional sites on the inside. The plasmid was derived by recombinant technology herein from parent vectors pLentiLox 3.7 (pLL3.7; Rubinson D A et al. Nature Genetics 33, 401-406 (2003) and pCMV-DsRed-Express (commercially available from BD Sciences Clontech, Mountain View Calif.) by replacing the GFP gene with DsRed. The siRNA-encoding hairpin DNA fragments expressed as in FIG. 3 are inserted into this vector, which is then used to produce lentivirus virion particles by co-transfection with appropriate packaging plasmids such as pHR-CMVΔ8.91 and pMD.G as shown below.

FIG. 5 is a drawing of three exemplary lentivirus packaging constructs: top is pCMVΔR 8.91 (Δenv+Δvif, Δvpu, Δnef); middle is envelope construct pMD.G, and bottom is transfer vector pRRLsin-CMV-GFP. These vectors are described, respectively, in Zufferey, R et al., Nat. Biotech. 15:871 (1997); Page, K A et al., J. Virol. 64:5270 (1990); and Zufferey, R et al. J. Virol. 71:9873 (1998).

Figure 8:
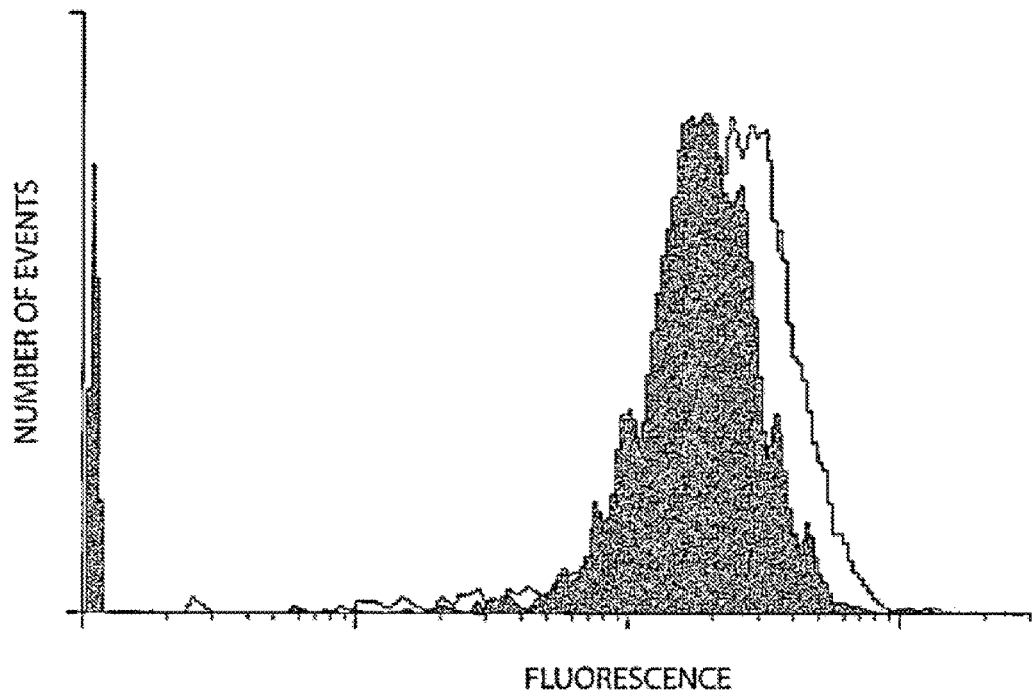

FIG. 8 is a graph comparing number of events, on the ordinate, and fluorescence, on the abscissa, in human 293 embryonic kidney cells stably transduced with lentivirus vectors expressing β2-microglobulin hairpin siRNA (left curve) or control vector (right curve), assayed by FACS using PE-conjugated anti-β2 antibody. Data show that lentivirus-mediated gene transfer of hairpin siRNA achieves inhibition of human β2-microglobulin on the cell surface in the entire population.

Figure 9:
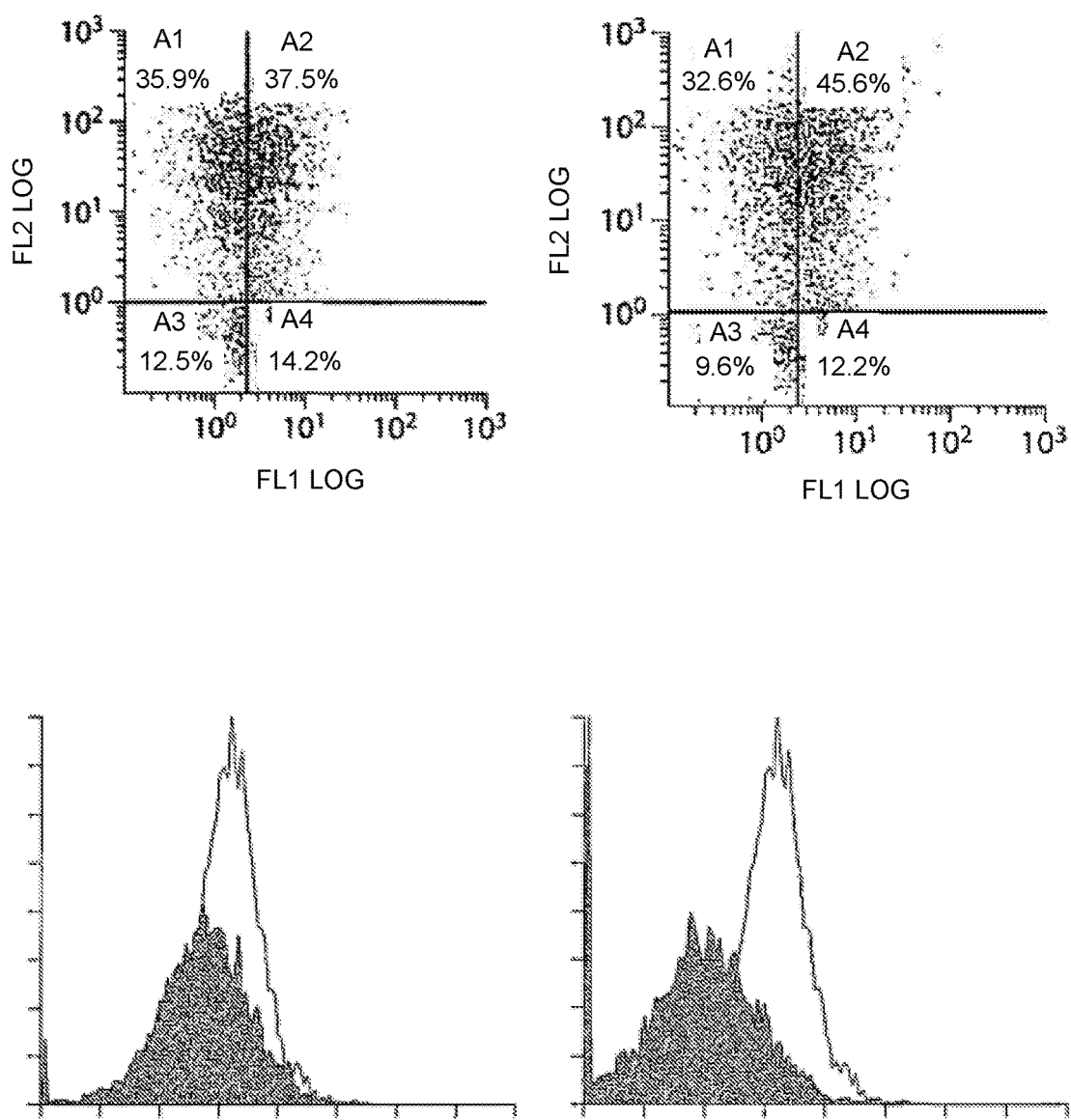

FIG. 9 is a set of graphs comparing number of events, on the ordinate, and fluorescence, on the abscissa, in human 293 embryonic kidney cells stably transduced with lentivirus vectors expressing universal sequence 1 (ABC-1; SEQ ID NO: 25) treated with hairpin siRNA (right curve) or control empty vector (left curve), assayed by FACS using PE-conjugated anti-α2 antibody. Data show that lentivirus-mediated gene transfer of hairpin siRNA achieves inhibition of human class I MHC A protein.

Figure 10:
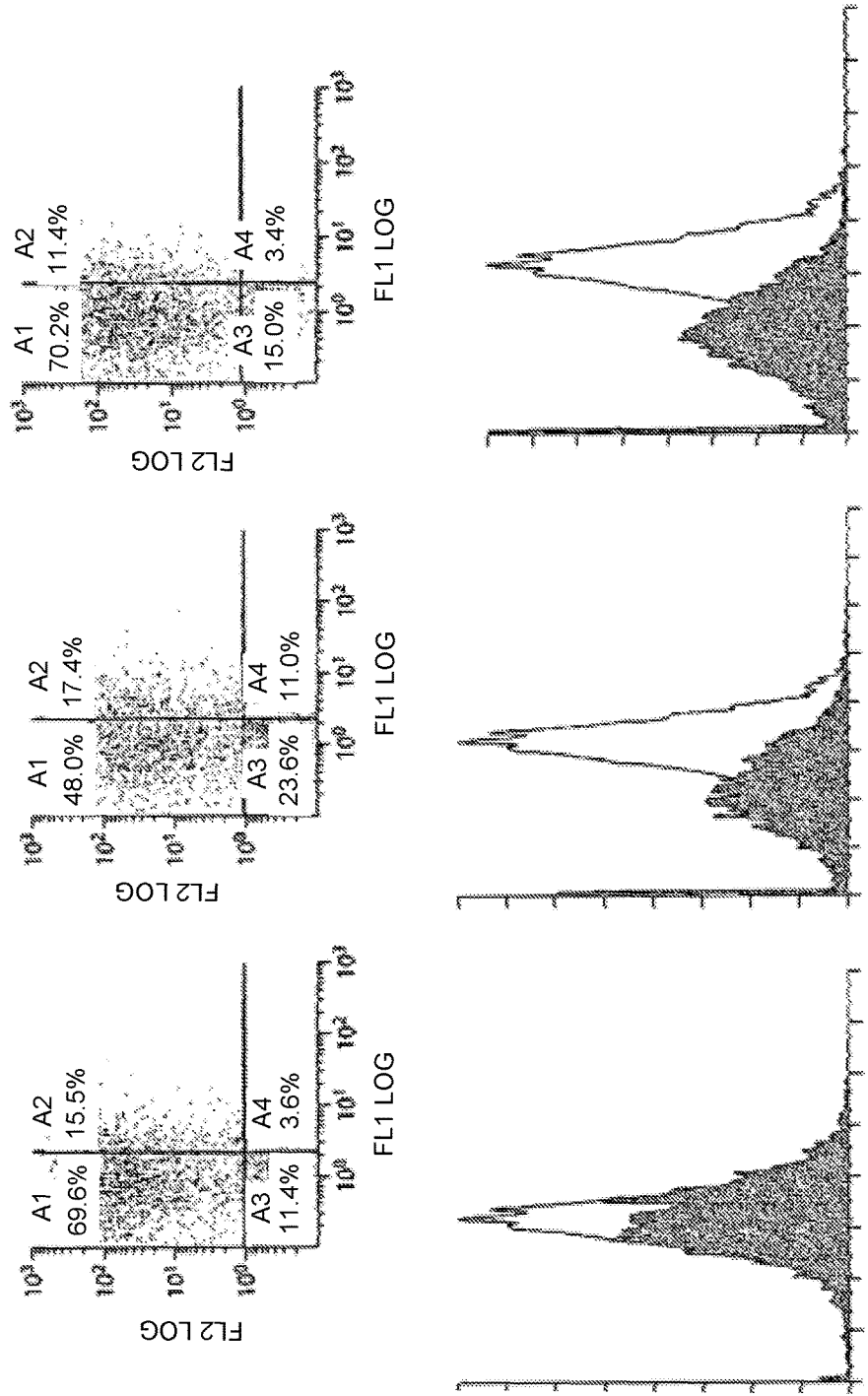

FIG. 10 is a set of graphs comparing number of events, on the ordinate, and fluorescence, on the abscissa, in human 293 embryonic kidney cells stably transduced with lentivirus vectors expressing universal sequence 1 (ABC-3; SEQ ID NO: 29) treated with hairpin siRNA (right curves) or control empty vector (left curve), assayed by FACS using PE-conjugated anti-□2 antibody. Data show that lentivirus-mediated gene transfer of hairpin siRNA achieves inhibition of human class I MHC A protein.

Figure 11:
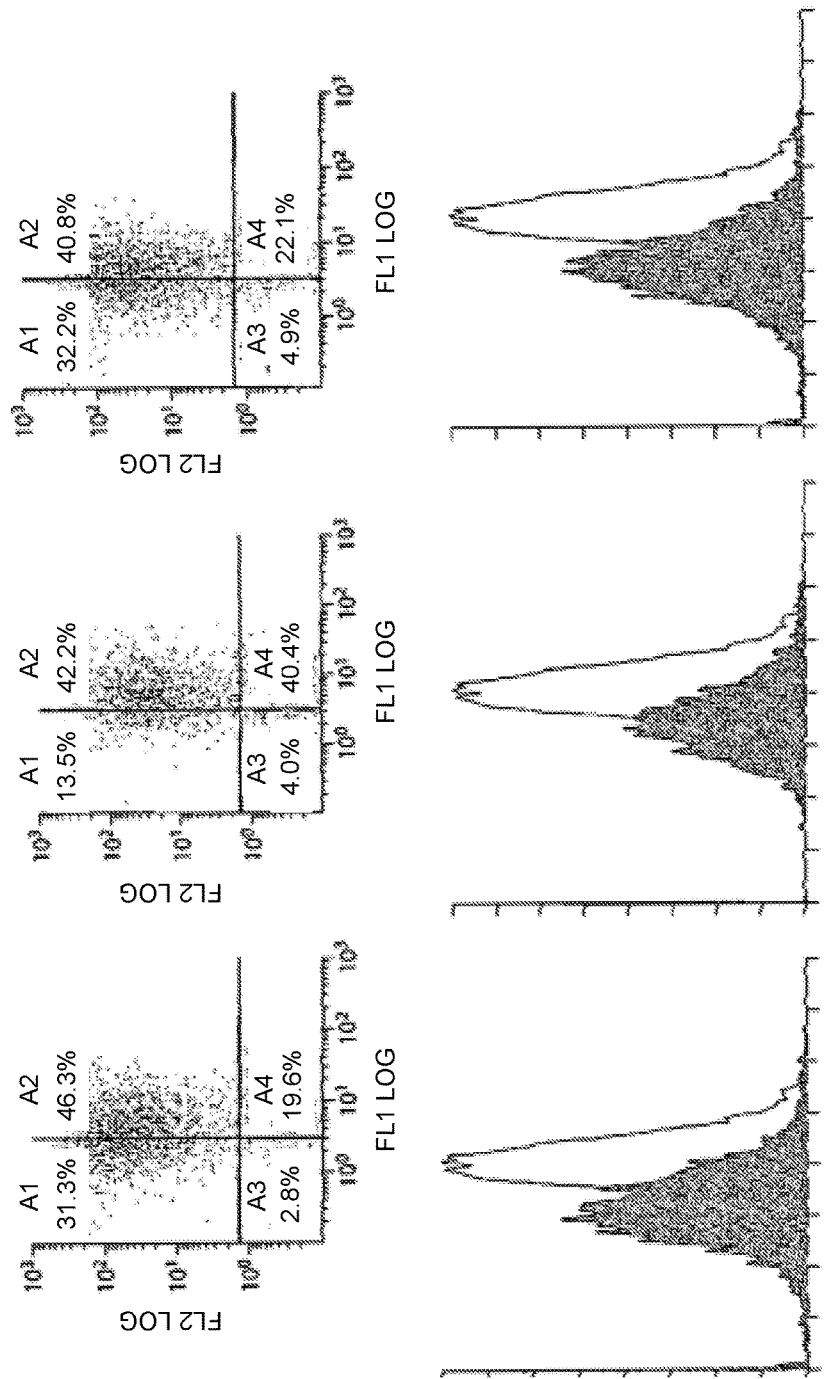

FIG. 11 is a set of graphs comparing number of events, on the ordinate, and fluorescence, on the abscissa, in human 293 embryonic kidney cells stably transduced with lentivirus vectors expressing universal sequence 1 (ABC-3; SEQ ID NO: 29) treated with hairpin siRNA (triplicate samples), assayed by FACS using PE-conjugated anti-α2 antibody reactive with each of A, B and C alleles respectively from left to right. Data show that lentivirus-mediated gene transfer of hairpin siRNA that is found in all three class I MHC alleles achieves inhibition of human class I MHC A, B and C proteins.

Figure 12:
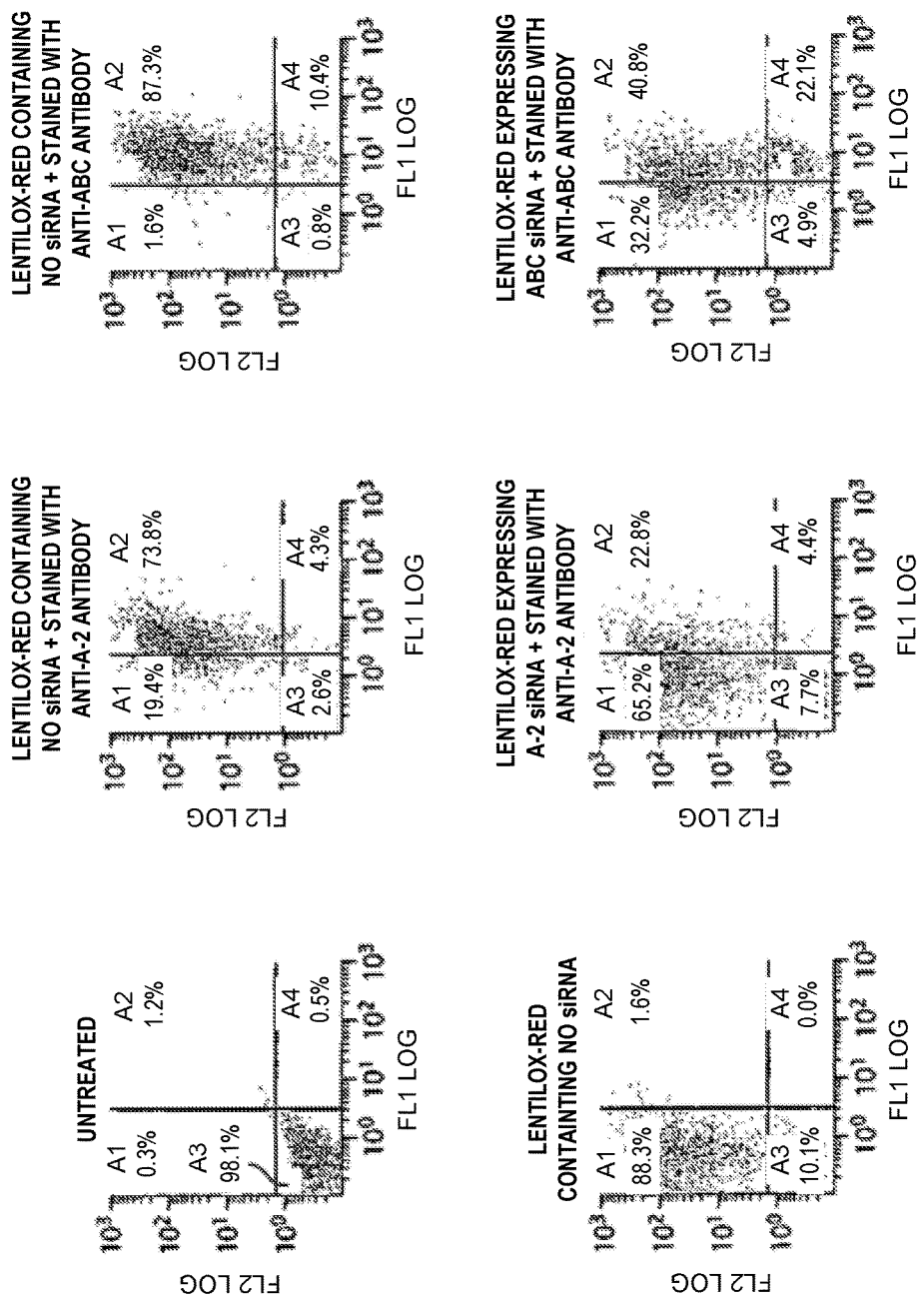

FIG. 12 is a set of graphs using human 293 embryonic kidney cells, showing FACS analysis of uninfected untransduced cells in the top left panel; empty-vector (no-siRNA) Lentilox-Red infected cells stained with anti-A-2 allele antibody in the top middle panel; empty-vector (no-siRNA) Lentilox-Red infected cells stained with anti-A, B and C locus antibody in the top right panel; Lentilox-Red empty vector infected unstained cells in the lower left panel; LentiLox-Red expressing A-2 siRNA stained with anti-A-2 antibody in the lower middle panel; and Lentilox-Red expressing ABC siRNA stained with anti-A, B and C locus antibody in the lower right panel. The data show a very major shift of cells into the quadrants that show no expression of the HLA proteins in the lower middle and right panels, indicating that siRNA inhibits expression of A-2 as shown in the lower middle panel, and all of A, B and C loci encoded proteins, as shown in the lower right.

Figure 13:
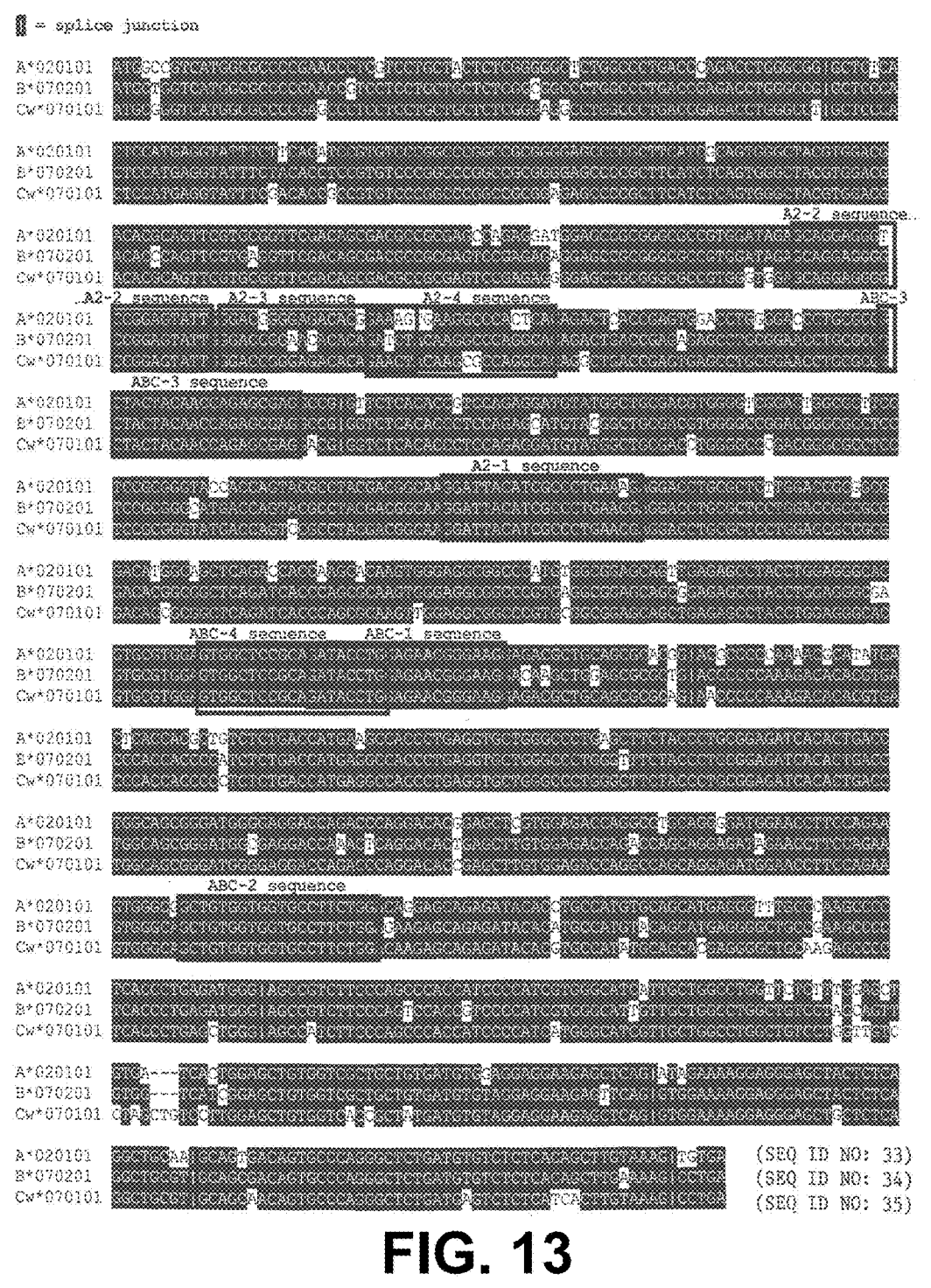

FIG. 13 shows alignment of the most common alleles of each human MHC Class I locus (mRNA sequences) where FIG. 13 represents an alignment of the sequences of the most common human MHC class I A, B, and C locus alleles in the Caucasian population where the alignment was used to determine which stretch of sequences, particularly within the a3 domains of each MHC locus, was highly conserved or highly divergent between each allele where, for targeting with siRNAs, we selected and tested both sequences common to all of these MHC I A, B and C loci alleles (ABC-1,2,3,4 sequences, shown in boxes), as well as sequences specific to the A locus of human MHC I (A2-1,2,3,4 sequences, shown in boxes); noting other sequences may also be chosen based on common or divergent stretches of approximately 20 base pairs, as revealed by sequence alignment performed as shown between these alleles or other MHC alleles.

Figure 14:
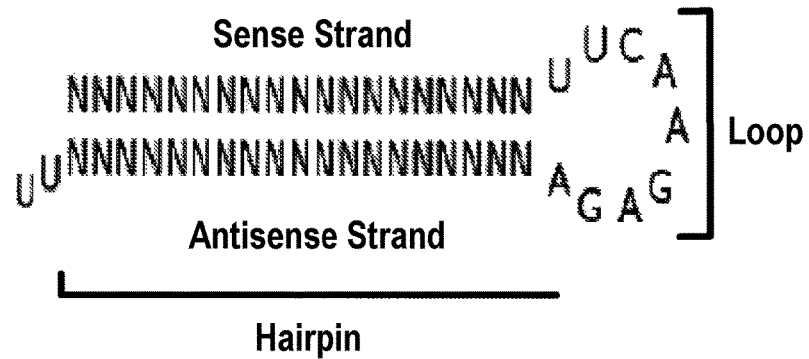

FIG. 14 shows Table 2, where Tables 1 and 3 are shown in the Appendix, where Table 2 shows sequence incorporation into hairpin siRNA constructs.

DETAILED DESCRIPTION OF THE EMBODIMENTS

HLA matching is more or less effective depending on the organ transplanted, and is a crucial procedure for maximizing the compatibility between the donor graft and the recipient. However, this necessarily means that the better the match between the donor tissues and the recipient, the more limited will be the supply of donors; in fact, identifying and procuring the best matches represents the major limitation to the field of organ transplantation, and the current situation is that there is an overwhelming lack of donors compared to the number of potential recipients, who must generally remain on a waiting list for a suitable match. Often no match can be obtained before the candidate recipient succumbs to their underlying disease.

Furthermore, even with well-matched HLA antigens, this procedure at best simply delays the ultimate onset of rejection, even in combination with potent general immunosuppressive treatments. While non-specific immunosuppression thus does enhance graft survival, the broad "shotgun" immunosuppressive regimens in current use remain risky in order to maintain a fine balance between "too little" immunosuppression resulting in graft rejection, or "too much" immunosuppression subjecting the transplant recipient to infection and toxicity. It should also be noted that, without specific immunosuppression methods to eliminate only the responding clones of cells that react against the donor mismatched antigens, a tolerance state can be achieved.

The present invention in one embodiment therefore provides a method to achieve such specific immunosuppression by down-regulating critical molecules (including, but not limited to, HLA) which participate in the process of host immune recognition of mismatches and/or activation of the immune response against the graft. Thus, immune cells responding to mismatched antigens in the donor are not generated or are specifically modulated, thereby reducing or eliminating the need for HLA matching in order to achieve specific non-responsiveness to the donor antigens. Furthermore, simply from the standpoint of avoiding the development of HLA antibodies, it would be advantageous to down-regulate their expression on the cell surface of the transplant graft, thereby denying any such antibodies a target.

This is achieved by the use of virus-based gene delivery vehicles, or "vectors", which allow efficient and stable transduction of donor graft cells. The virus vectors (embodiments for long-term stable transduction include, but are not limited to, lentivirus vectors, adeno-associated virus (AAV) vectors, and helper-dependent adenovirus vectors) are employed to deliver nucleic acid sequences that down-regulate or interfere with the function of mRNAs encoding critical immune recognition or activation proteins, or that encode proteins which in turn down-regulate or otherwise interfere with the function of the above-mentioned mRNAs encoding critical immune recognition or activation proteins. The first method includes, but is not limited to, the delivery of sequences encoding small interfering RNAs (siRNAs), anti-sense mRNA, and ribozymes. The second approach includes, but is not limited to, the delivery of sequences encoding specific ubiquinating enzymes, dominant-negative inhibitory proteins, and transmembrane or secreted immunosuppressive factors. The targets for these inhibitory sequences include, but are not limited to, HLA antigens, co-stimulatory molecules, and immuno-inhibitory signaling receptors. The net effect is to decrease donor cell immunogenicity and reduce the recipient's immune response.

Lentiviral Vectors

Although the life cycle of lentiviruses is similar to that of oncoretroviruses, there are several major differences. Vectors based on oncoretroviruses such as Moloney murine leukemia virus (MLV), which have hitherto been the most popular gene delivery system used in clinical trials, can only transduce cells that divide shortly after infection, because the MLV pre-integration complex cannot migrate to the nucleus in the absence of nuclear envelope breakdown during mitosis.

Lentiviruses such as HIV can infect non-proliferating cells, owing to the karyophilic properties of the lentiviral pre-integration complex which allows recognition by the cell nuclear import machinery. Correspondingly, HIV-derived vectors can transduce cell lines that are growth-arrested in culture, as well as terminally differentiated primary cells including neurons, hepatocytes, and cardiomyocytes, endothelium, alveolar pneumocytes, and keratinocytes (Naldini et al., 1996 Science 272: 263-267; Blomer et al., 1996 Hum. Mol. Genet. 5: 1397-1404; Kafri et al., 1997 Nature Genet. 17: 314-317; Sakoda et al., 1999 J. Mol. Cell. Cardiol., 31: 2037-2047; Shichinohe et al., 2001; Borok et al., 2001 J. Virol. 75: 11747-11754; Li et al., 2002 Exp. Cell Res. 273: 219-228; Chen et al., 2002 Nature Genet. 32: 670-675).

Figure 5:
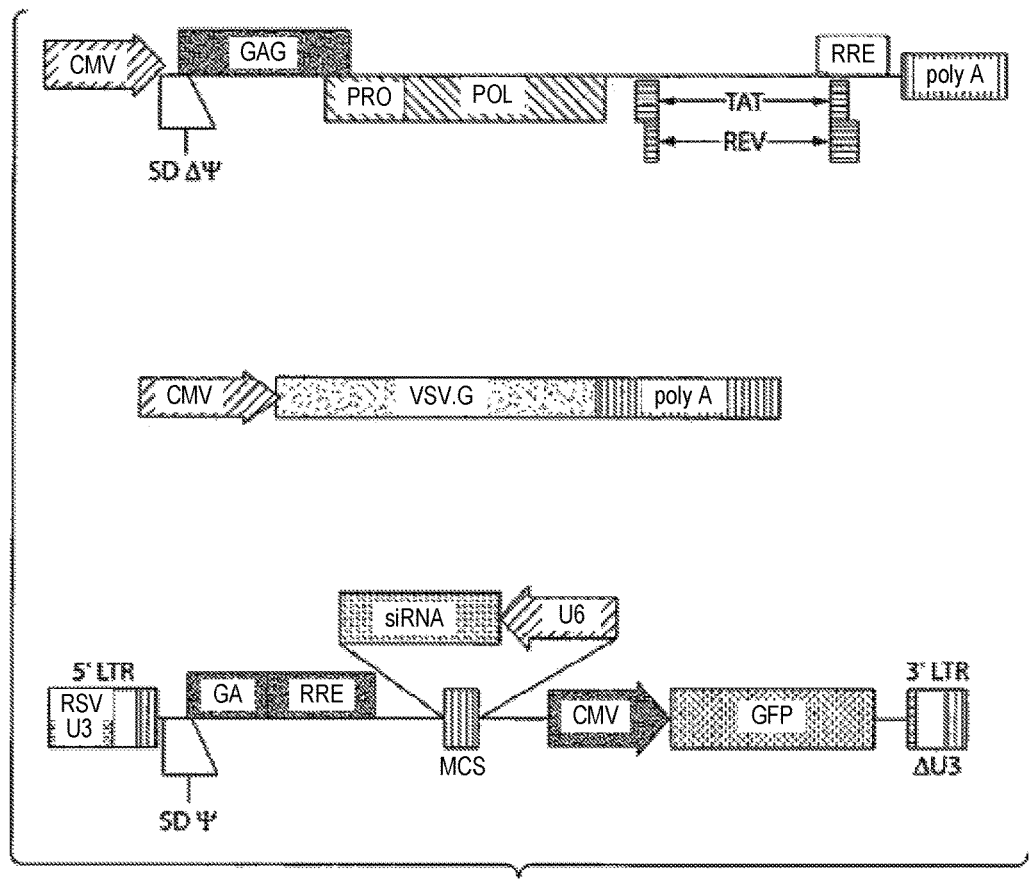

Pseudotyped lentiviral vectors have also been shown to mediate efficient delivery, integration, and sustained long-term expression of transgenes into post-mitotic cells such as adult neurons in vivo (Naldini et al., Science 272: 263-267 1996; Blomer et al., 1996 Hum. Mol. Genet. 5: 1397-1404). In this case, the vector was pseudotyped (i.e., encoated with a heterologous envelope protein) with vesicular stomatitis virus glycoprotein (VSV-G) to achieve wider host range and stability of virions. VSV-G pseudotyped vectors can be concentrated up to 109 infectious particles per ml; however, the possible toxicity of vector preparations containing the highly fusogenic VSV-G protein remains a concern, especially at higher multiplicities of infection. Furthermore, the possible toxicity of HIV accessory genes retained in lentiviral vector constructs, as well as the possibility of recombination leading to generation of wild type virus, has also been raised as a safety concern. HIV-derived multiply attenuated vector systems deleted of vif, vpr, vpu, nef and tat have been reported (Zufferey et al., 1997 Nature Biotechnol. 15: 871-875; Dull et al., 1998 J. Virol. 72: 8463-8471). The only auxiliary gene remaining in this system is rev, which, along with the Rev response element (RRE) as its cognate binding sequence, is required for efficient export of the vector and packaging construct RNAs from the nucleus during virus production (FIG. 5). Thus both toxicity and the likelihood of recombination are reduced in these second- and third-generation lentiviral vector systems.

Another advantage of lentiviral vector systems is that the promoter inherent in the HIV long terminal repeat (LTR) is critically dependent on the HIV-encoded Tat transctivator protein for transcriptional function. As the sequences encoding Tat are completely removed from the lentiviral vector construct, there is little promoter activity from the LTR, and effective transgene expression is dependent on the addition of an internal promoter. Although our lentiviral constructs all currently contain internal CMV promoters to drive transgene expression (see below), this dependence on internal promoters would be particularly advantageous if tissue-specific (e.g., neuron-specific) or conditional (e.g., tetracycline-responsive) promoters were to be used. This may also be important for long term gene expression, as silencing of CMV promoter-driven transgene expression has been described over time in some cells. Furthermore, it has previously been found that, despite the lack of significant promoter activity in the absence of Tat, promoter interference between the HIV LTR and the internal CMV promoter can occur, thus significantly attenuating the levels of transgene expression achieved. This has been largely overcome by the use of third-generation self-inactivating (SIN) vectors, in which a portion of the U3 region of the 3' LTR has been deleted (Dull et al., 1998 J. Virol. 72: 8463-8471); thus, after reverse transcription, this deletion will be copied to the 5' LTR and hence result in loss of LTR promoter sequences in the integrated provirus, which therefore prevents interference with the function of the internal promoter.

Vector System

An HIV-based packaging system for the production of lentiviral vectors is employed herein (FIG. 5), using constructs in Naldini et al., 1996 Science 272: 263-267; Zufferey et al., 1997 Nature Biotechnol. 15: 871-875; and Dull et al., 1998 J. Virol. 72: 8463-8471.

The lentivirus packaging construct pCMVΔR 8.91 contains the HIV gag-pol genes driven by a CMV promoter, with both the packaging signal and most of the env gene deleted (except for the RRE and the Tat and Rev coding sequences), and is deleted of vif, vpr, vpu, and nef (Zufferey et al., 1997 Nature Biotechnol. 15: 871-875). To replace the HIV gp160 envelope (which would result in a vector that binds only CD4+ cells), we use the envelope construct pMD.G, which expresses the vesicular stomatitis virus glycoprotein envelope (VSV-G; Naldini et al., 1996 Science 272: 263-267); this allows efficient transduction of a wide variety of cell types, as the receptor for VSV-G is thought to be a phospholipid.

A number of vector constructs are available to be packaged using the above system, based on the third-generation lentiviral SIN vector backbone (Dull et al., 1998 J. Virol. 72: 8463-8471). For example the vector construct pRRLsinC-MVGFPpre contains a 5' LTR in which the HIV promoter sequence has been replaced with that of Rous sarcoma virus (RSV), a self-inactivating 3' LTR containing a deletion in the U3 promoter region, the HIV packaging signal, RRE sequences linked to a marker gene cassette consisting of the *Aequora* jellyfish green fluorescent protein (GFP) driven by the CMV promoter, and the woodchuck hepatitis virus PRE element, which appears to enhance nuclear export.

Figure 3:
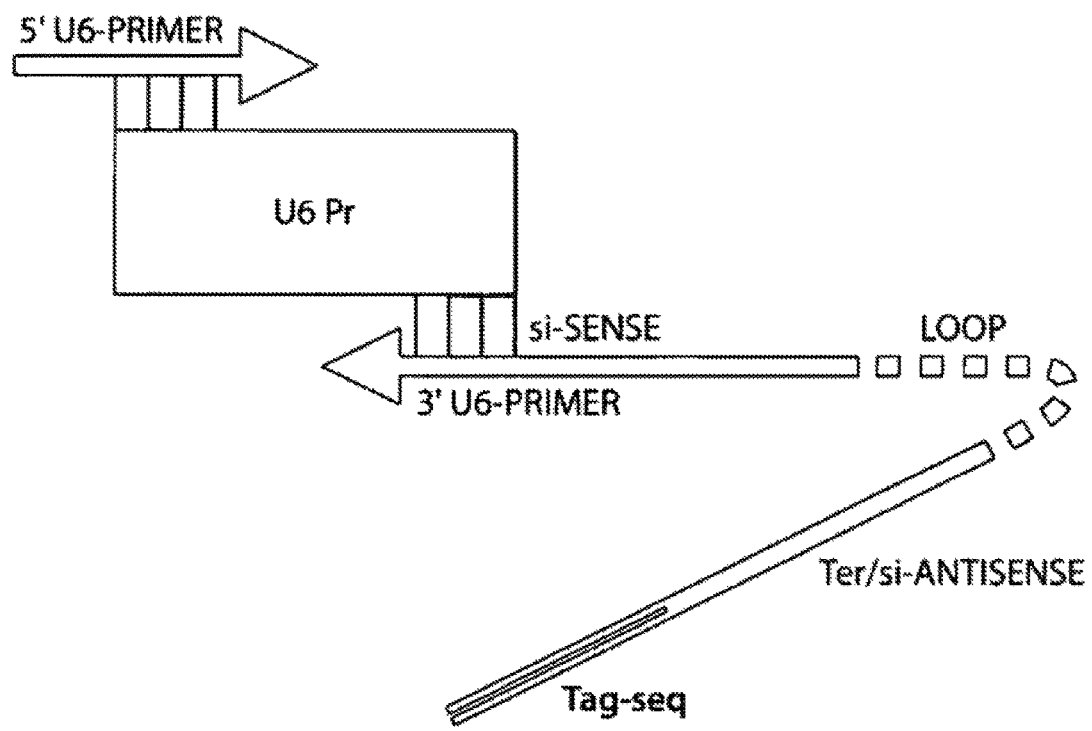

The GFP marker gene allows quantitation of the transduction efficiency simply by UV fluorescence microscopy or flow cytometry (Kafri et al., 1997 Nature Genet. 17: 314-317; Sakoda et al., 1999 J. Mol. Cell. Cardiol., 31: 2037-2047). Therefore, a version of pRRLsinCMVGFP was constructed that contains a multiple cloning site (MCS) just upstream of the CMV-GFP cassette, into which can be cloned the siRNA expression cassette. For expression of siRNA in examples herein, the U6 promoter (a Pol III-type promoter) is used instead of the CMV promoter (a Pol II-type promoter), as shown in FIG. 3. The U6 promoter-siRNA hairpin cassette can be constructed and inserted by one-step amplification by PCR using an upstream primer containing a restriction site in the MCS contiguous with a sequence targeting the 5' end of the U6 sequence and a downstream primer that contains another restriction site in the MCS, and the complementary sequence of the complete hairpin contiguous with the 3' end of the U6 sequence. Alternatively, the U6 promoter can first be cloned into the MCS by itself, followed by insertion of cDNA for the siRNA sequence (consisting of a DNA oligonucleotide containing a portion of the sequence of the targeted gene, a hairpin loop structure, and the targeted sequence in reverse orientation, annealed to a second oligonucleotide containing sequences that are complementary to the first oligonucleotide) downstream of the promoter.

Alternatively, commercially available lentiviral vectors such as pLentilox can also be used. The pLentilox vector construct already contains a GFP marker gene cassette, was used herein to construct a derivative, pLentiLox-Red (FIG. 4), which has a U6 promoter inserted into the vector and a MCS with unique Hpa I and Xho I sites available to insert siRNA-encoding hairpin sequences. The result is a plasmid having replaced the GFP marker gene in pLentilox with the marker gene dsRed (FIG. 4), which expresses a red fluorescent protein.

The lentiviral vector construct containing the U6-siRNA hairpin cassette is transiently co-transfected along with the pCMVΔR 8.91 gag-pol packaging construct and pMD.G env construct into 293T cells to produce virus (FIG. 5). This transient transfection system enables high level expression of viral proteins and efficient packaging of vector genomes without the need for long-term maintenance of stable packaging cell lines and thus without the attendant risk of recombination leading to generation of helper virus over time. Lentiviral vector packaging systems are commercially available (e.g., Virapower lentiviral vector production kit, Invitrogen, Carlsbad Calif.). The virus supernatants are harvested, filtered through a 0.45 μm syringe filter, and used to transduce target cells.

As the presence of free VSV-G envelope proteins as a contaminant in the vector preparations during transduction of the target cells because certain cell types are sensitive to the toxicity of the highly fusogenic VSV-G protein, the free VSV-G protein is cleared from the preparation by means of centrifugation through a 300 kDa MW cut-off filter. Thus, most free proteins including the VSV-G protein will spin through the filter, while the purified virus will remain in the retentate. This procedure will also serve to concentrate the vector preparation in the event that the titers of the unconcentrated preparations result in inadequate gene transfer efficiency.

Pharmaceutical Compositions

In one aspect of the present invention, pharmaceutical compositions comprising a lentivirus-treated tissue or cell population are provided, wherein these compositions optionally comprise a pharmaceutically acceptable carrier. In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), B vitamins such as biotin, and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., (1995) discloses various carriers used in formulating pharmaceutical compositions and known techniques for the preparation thereof. Some examples of materials which can serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

In yet another aspect, according to the methods of treatment of the present invention, the treatment of tissues or cells to reduce HLA expression with an engineered lentivirus and a pharmaceutical composition, as described herein. Thus, the invention provides methods for treatment comprising administering a therapeutically effective amount of a pharmaceutical composition comprising active agents that include siRNA or anti-sense RNA to a tissue or cells for administering a subject in need thereof, in such amounts and for such time as is necessary to achieve the desired result. It will be appreciated that this encompasses administering an inventive pharmaceutical as a therapeutic measure to promote the tissue graft associated with surgery or treatment. In certain embodiments of the present invention a "therapeutically effective amount" of the pharmaceutical composition is that amount effective for retention of a graft for a substantial fraction of a lifetime. The compositions, according to the method of the present invention, may be administered using any amount and any route of administration effective for treating the subject with the graft. Thus, the expression "amount effective for promoting the retention of the graft", as used herein, refers to a sufficient amount of composition to inhibit rejection. The exact dosage is chosen by the individual physician in view of the patient to be treated. Dosage and administration are adjusted to provide sufficient levels of the active agent(s) or to maintain the desired effect. Additional factors which may be taken into account include the severity of the disease state prior to receipt of the graft, e.g., extent of disease, history of the condition; age, weight and gender of the patient; diet, time and frequency of administration; drug combinations; reaction sensitivities; and tolerance/response to therapy.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total usage of the compositions of the present invention will be decided by the attending physician within the scope of sound medical judgment in terms of frequency of graft required by the subject. For any active tissue or cell, the therapeutically effective dose can be estimated initially in animal models, usually mice, rabbits, dogs, or pigs. The animal model is also used to achieve a desirable surgical procedure and/or route of administration. Direct application of the graft is dependent on the nature of the cell, tissue or organ. Such information is used to determine useful doses and additional routes for administration in humans. A therapeutically effective dose refers to that amount of that ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from animal studies is used in formulating a range of dosage for human use.

Administration of Pharmaceutical Compositions

After formulation with an appropriate pharmaceutically acceptable carrier in a desired dosage, the pharmaceutical compositions of this invention can be administered to humans and other mammals surgically such as ocularly in the case of corneal grafts (as by powders, ointments, or drops), i.e., as applied surgically to the eye. Alternative and additional routes such as intravenously in the case of stem cell grafts, or by abdominal surgery for tissue grafts, or thoracic surgery for heart or lung grafts.

Liquid dosage forms for ocular administration include buffers and solubilizing agents, preferred diluents such as water, and under some circumstances, preservatives such as thymosol, and one or more biopolymers or polymers for conditioning the solution, such as polyethylene glycol, hydroxypropylmethylcellulose, sodium hyaluronate, sodium polyacrylate or tamarind gum.

Dosage forms for ocular surgery of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular grafts may be treated with aqueous drops, a mist, an emulsion, or a cream. Administration may be therapeutic or it may be prophylactic. Prophylactic formulations may be present or applied to the site of potential grafts, and additional materials may be used such as eye drops, and surgical irrigation solutions. The invention includes opthalmological devices, surgical devices, audiological devices or products which contain disclosed compositions (e.g., gauze bandages or strips), and methods of making or using such devices or products. These devices may be coated with, impregnated with, bonded to or otherwise treated with a disclosed composition.

Injectable preparations of cells or treated tissues, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations of solutions prior to addition of cells can be sterilized, for example, by filtration through a bacterial-retaining filter, or by incorporating sterilizing agents in the form of sterile solid compositions which can be dissolved or dispersed in sterile water or other sterile injectable medium prior to addition of the cell graft.

Uses of Pharmaceutical Compositions

In general, it is shown herein that immunomodulated graft cells or tissues, such as corneal cells, are clinically useful in stimulating the healing associated with any graft including but not limited to the corneal epithelium; the lining of the gastrointestinal tract; the lung epithelium; and the inner surface of kidney tubules, of blood vessels, of the uterus, of the vagina, of the urethra, or of the respiratory tract. The present invention encompasses in various embodiments the treatment of a variety of epithelial wound types including but not limited to surgical wounds, excisional wounds, blisters, ulcers, lesions, abrasions, erosions, lacerations, boils, cuts, sores, and burns resulting from heat exposure or chemicals. These wounds may be in normal individuals or those subject to conditions which induce abnormal wound healing such as diabetes, corneal dystrophies, uremia, malnutrition, vitamin deficiencies, obesity, infection, immunosuppression and complications associated with systemic treatment with steroids, radiation therapy, non-steroidal anti-inflammatory drugs (NSAID), anti-neoplastic drugs and anti-metabolites.

Lentivirus treated epithelial cells are, for example herein, useful to promote dermal re-establishment subsequent to dermal loss. Suitable skin grafts include, but are not limited to, autografts, artificial skin, allografts, autodermic grafts, autoepidermic grafts, avacular grafts, Blair-Brown grafts, bone grafts, brephoplastic grafts, cutis grafts, delayed grafts, dermic grafts, epidermic grafts, fascia grafts, full thickness grafts, heterologous grafts, xenografts, homologous grafts, hyperplastic grafts, lamellar grafts, mesh grafts, mucosal grafts, Ollier-Thiersch grafts, omenpal grafts, patch grafts, pedicle grafts, penetrating grafts, split skin grafts, and thick split grafts.

Grafts are useful herein to treat epidermolysis bullosa, a defect in adherence of the epidermis to the underlying dermis which results in frequent, open and painful blisters, by accelerating re-epithelialization of these lesions. Grafts are further useful to treat pemphigus diseases that involve loss of cell-cell adhesion within the epidermis, or pemphigoid diseases that involve loss of cell-cell adhesion at the dermo-epidermal junction.

The present invention provides vectors and methods for treating donor cells for grafts into recipient subjects of a variety of organs and tissues, of which corneal tissue can be considered exemplary. Conditions to be treated using the methods and vectors provided herein include: corneal epithelial defects caused by corneal ulcers, heat, radiation, phlyctenulosis, corneal abrasions or lacerations, photorefractive surgery for corrective myopia, foreign bodies and sterile corneal infiltrates; chemical burns caused by exposure to acids or alkali (e.g., hydrofluoric acid, formic acid, anhydrous ammonia, cement, and phenol) or other chemical agents such as white phosphorus, elemental metals, nitrates, hydrocarbons, and tar; keratopathies such as neurotrophic keratopathy, diabetic keratopathy and Thygeson's superificial punctate keratopathy; keratities such as viral keratitis (e.g., metaherpetic or herpetic keratitis) and bacterial keratitis; and corneal dystrophies such as lattice dystrophy, epithelial basement membrane.

The present invention also provides vectors and methods for treating donor cells for grafts into recipient subjects, of which bone marrow cells and hematopoietic stem cells can be considered exemplary. Conditions to be treated using the methods and vectors provided herein include: various hemoglobinopathies, including but not limited to sickle cell anemia and thalassemias, various other hereditary defects manifested as diseases of red blood cells, such as pyruvate kinase deficiency, or diseases of white blood cells, such as severe combined immunodeficiency (SCID).

EXAMPLES

Methods of the Invention

A method for long-term immune evasion by viral gene transfer-mediated pre-conditioning of donor graft cells, is provided. In accordance with this method a vector for expression of an siRNA or an antisense is constructed, and includes the following: selecting at least one immune recognition or activation protein as targets; identifying one or more target sequences (either conserved non-polymorphic sequences for general inhibition, or polymorphic sequences for specific inhibition) in the target proteins; designing inhibitory sequences directed against above conserved target sequences, according to established principles; and constructing and producing virus vectors (e.g., lentivirus vectors) expressing inhibitory sequences.

For an alternative approach, the selected target proteins in the donor graft cells are to be inhibited directly by expression of a heterologous protein (e.g., HIV nef protein, HTLV p12 protein, E3 protein from adenovirus serotype 5, etc. can directly down-regulate HLA) in these cells, or alternatively, immunosuppressive proteins may be expressed from the graft cells which result in direct inactivation or elimination of responding immune effector cells (e.g., TGFβ, FasL, HLA-G). In this case, there is no need for identification of target sequences or design of inhibitory sequences (i.e., steps 2 and 3), and instead the inhibitory protein coding sequences can simply be inserted into a suitable viral expression vector for subsequent production and graft transduction by one of ordinary skill in the art.

Immuno-inhibitory virus vectors thus generated are used to achieve efficient and stable gene transfer to the donor graft cells ex vivo, thus providing the graft with a mechanism for long-term evasion from the host immune response. As specified above, the preferred embodiments of the present invention for virus vectors capable of achieving long-term stable transduction include, but are not limited to, lentivirus vectors, adeno-associated virus (AAV) vectors, and helper-dependent adenovirus vectors. The use of immuno-inhibitory lentiviral vectors will be illustrated below in examples which demonstrate a preferred method for practicing the invention. However, these examples are not exhaustive and other embodiments of this method may be employed without undue experimentation by one of ordinary skill in the art.

Recombinant Methods for Insertion of Sequences into Vector and Transfection into Cells SEQ ID NOs: 1-14 such as "ABC-1" refer to targeted sequences obtained that satisfy the criteria herein, and are located in mRNA transcribed from the gene of the targeted protein. Further, the targeted sequences define both the forward and reverse sequence oligonucleotide sequences used for cloning. The "forward" sequence represents an oligonucleotide that consists of the approx. 20 nucleotide MHC target sequence plus the loop plus the complementary sequence to the prior 20 nucleotide MHC target sequence, such that, when transcribed into RNA, it can fold back on itself, such that the complementary "TGTAATCC" sequence can hybridize with the target "GGATTACA" sequence to form the hairpin structure ("C"s match up with "G"s, "T"s match up with "A"s, and vice versa, according to standard Watson-Crick complementary base pairing rules). However, the forward sequence by itself, although it defines the complete hairpin, only consists of a single strand oligonucleotide sequence. So, in order to clone it into the lentiviral vector plasmid, the forward sequence is paired with the "reverse" sequence. With respect to pairs of sequences listed as SEQ ID NOs: 17-32 in Table 3, for each SEQ ID labeled as "forward", the "reverse" sequence comprises a second oligonucleotide that is complementary to the forward sequence, so it can hybridize with the forward sequence oligonucleotide to form a double-stranded DNA fragment for insertion into the lentiviral vector (into a cloning site that is immediately downstream of the U6 promoter).

Further, the forward and reverse sequences are complementary except for the loop structure and the 5' and 3' ends. Finally, in order to clone into the Hpa I and Xho I sites in the vector plasmid, the 5' end and 3' end sequences are enzymatically treated to create a blunt end (to match up with the blunt end formed by digestion of the plasmid with Hpa I), and the other makes a staggered end with a 5' overhang (when hybridized with the forward oligo, the reverse oligo's 5' end is hanging out further than the forward oligo's 3' end, to form a single-stranded end piece, which can match up and hybridize with the staggered end formed by the Xho I cut site in the plasmid).

The forward and reverse siRNA hairpin-encoding DNA oligonucleotide sequences were annealed together to form a double-stranded DNA fragment that was then inserted into the pLentiLox-Red lentiviral vector plasmid (shown in FIG. 4) downstream from the U6 promoter by cleavage of the Hpa I and Xho I sites with the respective restriction endonucleases and ligation of the hairpin-encoding DNA fragment.

The pLentiLox vector plasmid (FIG. 3) with the inserted siRNA sequence was co-transfected into 293T cells with an appropriate packaging plasmid (FIG. 5), in order to produce lentivirus particles. For this lentiviral vector production step, a number of packaging plasmid systems and published protocols are available and any of these can be employed. Vectors suitable for the methods herein are reviewed in Wolkowicz, R et al., Methods Mol. Biol. 246:391-411 (2004), Curran M A et al. Mol. Ther. 1(1): 31-38 (2000), Follenzi et al., Human Gene Ther. 13:243-260 (2002), and Naldini L et al. Proc Natl Acad Sci USA 93(21): 11382-11383 (1996); those used for recombinant constructions as described herein are vectors in Zufferey, R et al., Nat. Biotech. 15:871 (1997); Page, K A et al., J. Virol. 64:5270 (1990); and Zufferey, R et al. J. Virol. 71:9873 (1998).

The resultant virus preparation will, upon infection of target cells, result in delivery of both the siRNA transgene as well as a CMV promoter-driven marker gene cassette expressing the red fluorescent protein dsRd. Thus, successfully transduced cells will show reduction of MHC levels due to expression of the siRNA, which can be detected as a reduction in mean fluorescence in the green wavelength channel upon binding a MHC-specific antibody conjugated with fluorescein isothiocyanate (FITC). Concomitantly, these cells will also show an increase in mean fluorescence level due to co-expression of the dsRed marker gene.

Example 1

Selecting Critical Immune Recognition or Activation Proteins as Targets

Figure 1:
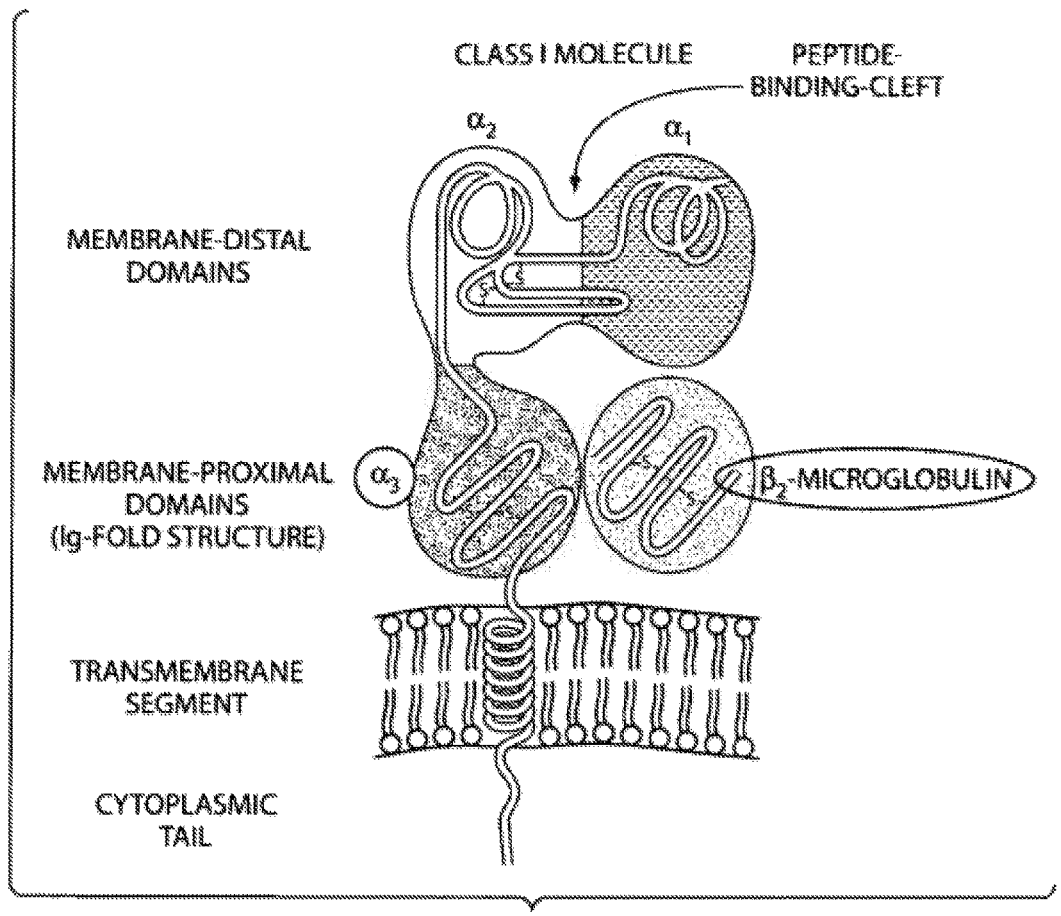
Figure 2:
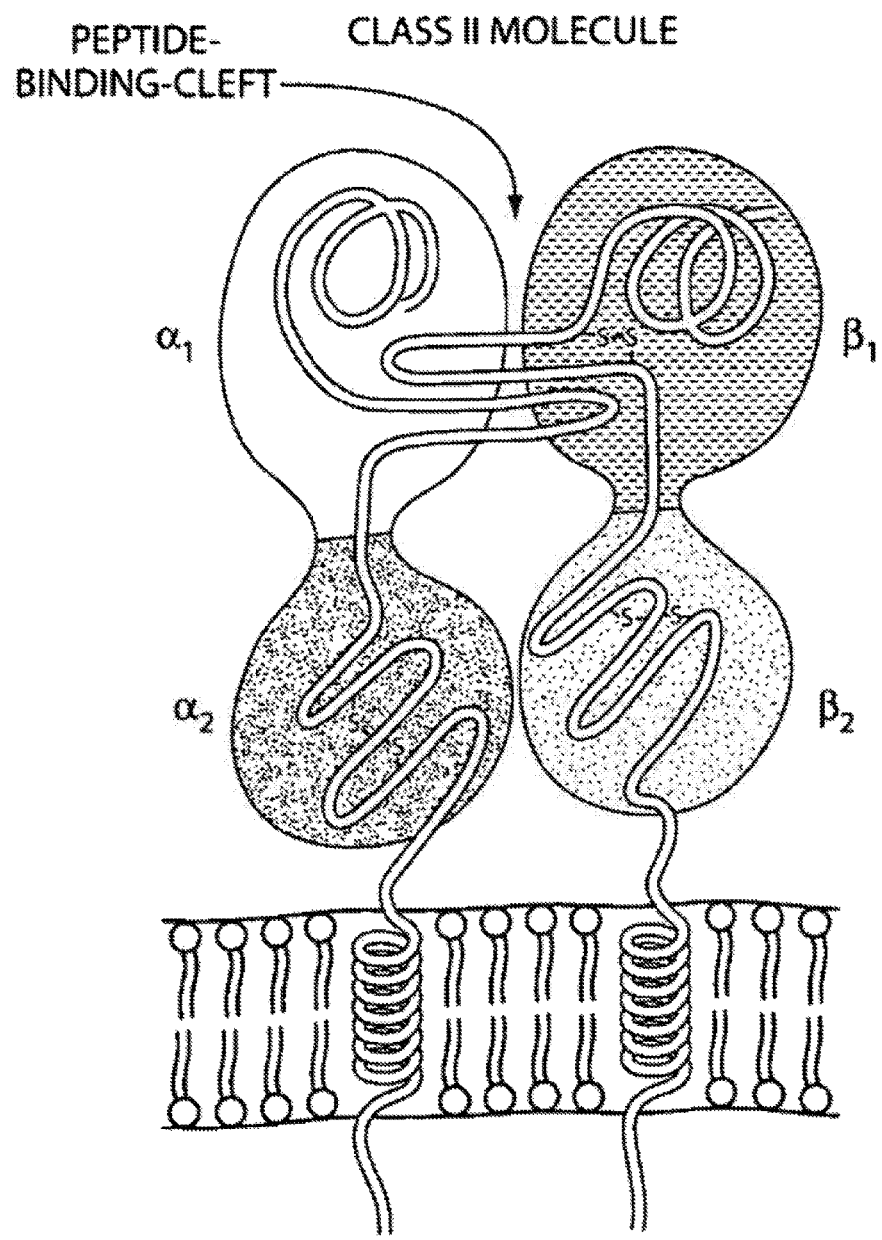

As mismatched HLA antigens are critical in evoking robust immune responses that attack donor cells, down-regulation of these antigens is used to eliminate any issue of matching or mismatching, thus beneficial for enhancing graft survival. In particular, from the above information regarding the relative importance of different HLA antigen loci in transplant graft rejection, the preferred HLA antigen targets are the Class I antigens HLA-A and -B (FIG. 1), and the Class II antigen-DR (FIG. 2). All exons of each may contain sequences that are useful for construction of siRNA or antisense. Further, these target proteins are not necessarily the only targets available, and other targets also include, but are not limited to, immunostimulatory co-activators such as CD80 (B7.1), CD86 (B7.2), etc. which may also be expressed on the surface of certain donor graft cells.

Example 2

Identifying Target Sequences (Conserved Non-Polymorphic Sequences for General Inhibition or Polymorphic Sequences for Specific Inhibition) in the Target Proteins HLA antigens are highly polymorphic; indeed, this is the very reason for the need to match HLA types between donor and recipient. However, certain regions within the HLA sequence are highly conserved and non-polymorphic; if targeted, these regions allow global inhibition of HLA expression in the donor cells regardless of the specific HLA type of the donor. HLA Class I antigens share the same general structure, being composed of a heavy chain consisting of three alpha ($\alpha$) domains, which are noncovalently paired with a smaller chain known as beta-2 ($\beta$2)-microglobulin (FIG. 1). The heavy chain and $\beta$2-microglobulin associate with each other, along with antigenic peptides, in the endoplasmic reticulum, and are transported together to the cell surface. In particular, the $\alpha$3 domain has a non-polymorphic loop that interacts with CD8, and the $\beta$2-microglobulin subunit is invariant. These are the preferred target sequences in this particular embodiment of the invention.

For down-regulation of a specific HLA antigen to nullify a mismatch at a particular HLA locus in an otherwise well-matched donor graft, the highly polymorphic sequences in the $\alpha$1 domain or $\alpha$2 domain of the HLA Class I antigens is targeted. Many HLA antigens have been sequenced, hence one of ordinary skill in the art can identify the appropriate target sequences for inhibition of a specific HLA allele. Thus, for example, if a donor graft is well matched at both alleles in the HLA-B and -DR loci, and is matched at one allele in the HLA-A locus but is mismatched at the other (i.e., a 5 out of 6 match), the $\alpha$1 and $\alpha$2 domain sequences of the specific HLA-A allele that is mismatched in the donor can be determined from a search of available HLA sequences, and these unique sequences would be used to target only this particular antigen for suppression in the donor graft cells, thereby essentially converting the graft into a "5 out of 5" perfect match which would significantly enhance graft survival.

A strategy for targeting MHCs using siRNA or antisense RNA includes identifying target domains of MHC molecules. A suitable stretch of coding mRNA for targeting by siRNA or antisense RNA has the following properties: secondary structures do not appear that would hinder silencing; there must be a minimum of non-identity, as a single nucleotide that is non-complementary might abolish silencing; the cDNA nucleotide sequence must begin with a Guanine since that base is the start site of the U6 promoter. Guidelines of properties for efficient siRNA further include: length of 21 to 23 nucleotides as a length of double stranded RNA greater than 30 triggers interferon response and cell death; the G+C content must be about 50%; and cDNA sequences preferably conform to the following, in order of preference: AA(N19)TT>NA(N21)>-; NAR(N17)YNN, where N, Y and R are the conventional symbols for any nucleotide, a pyrimidine, and a purine, respectively.

Once suitable target sequences are identified, siRNA expression cassettes are constructed by PCT and inserted into a viral vector. The siRNA expression vectors are introduced into donor cells, resulting in functional expression if siRNA inside the cell. Silencing is assayed and confirmed by Northern blot, RT-PCR, Western blot, and/or FACS.

Example 3

Design of Inhibitory Sequences Directed Against Conserved Target Sequences

In this embodiment, several siRNA sequences directed against the non-polymorphic sequences in the HLA Class I β2-microglobulin subunit were designed. In general, appropriate sequences should adhere to existing guidelines for efficient siRNA-mediated silencing, including the use of 21 to 23 nt long siRNA sequences (as double-stranded RNAs of greater than 30 nucleotide lengths appear to trigger a non-specific interferon response resulting in global host protein synthesis shut-off), approximately 50% G/C-content, and corresponding cDNA sequences encoding the siRNA should be, in order of preference: AA(N19)TT>NA(N21)>NAR(-N17)YNN.

Such exemplary and non-limiting sequences in the human β2-microglobulin gene are shown in Table 2 and below:

```
                                   (SEQ ID NO: 6)
5'-GCCTTAGCTGTGCTCGCGCTACT-3'

(SEQ ID NO: 7)
5'-GAGGCTATCCAGCGTACTCCAAA-3'

(SEQ ID NO: 8)
5'-GTTTCATCCATCCGACATTGAAG-3'

(SEQ ID NO: 9)
5'-GTATGCCTGCCGTGTGAACCATG-3'

(SEQ ID NO: 10)
5'-GATAGTTAAGTGGGATCGAGACA-3'
```

The identified β2-microglobulin-derived sequences above and others, were screened by a BLAST homology search in GenBank (Table 1) to make determine whether the sequences share any identity or homology with sequences in other genes. Ideal sequences do not, as such homology would incur the potential risk of unintended down-regulation of such other genes, and this might be detrimental to the normal functioning of the donor cells. As shown in Table 1, SEQ ID NO: 1 of β-MG shares identity with positions 3015 to 3000 of human microtubule-associated protein 6 (SEQ ID NO: 36) and positions 1591-1606 of human myelin gene expression factor 2 (MEF-2, SEQ ID NO: 37).

Candidate sequences that showed significant homology to non-HLA genes were discarded, only those which are unique to the HLA antigen are employed, therefore additional sequences were obtained (SEQ ID Nos: 2-6 above and Table 2).

Figure 4:
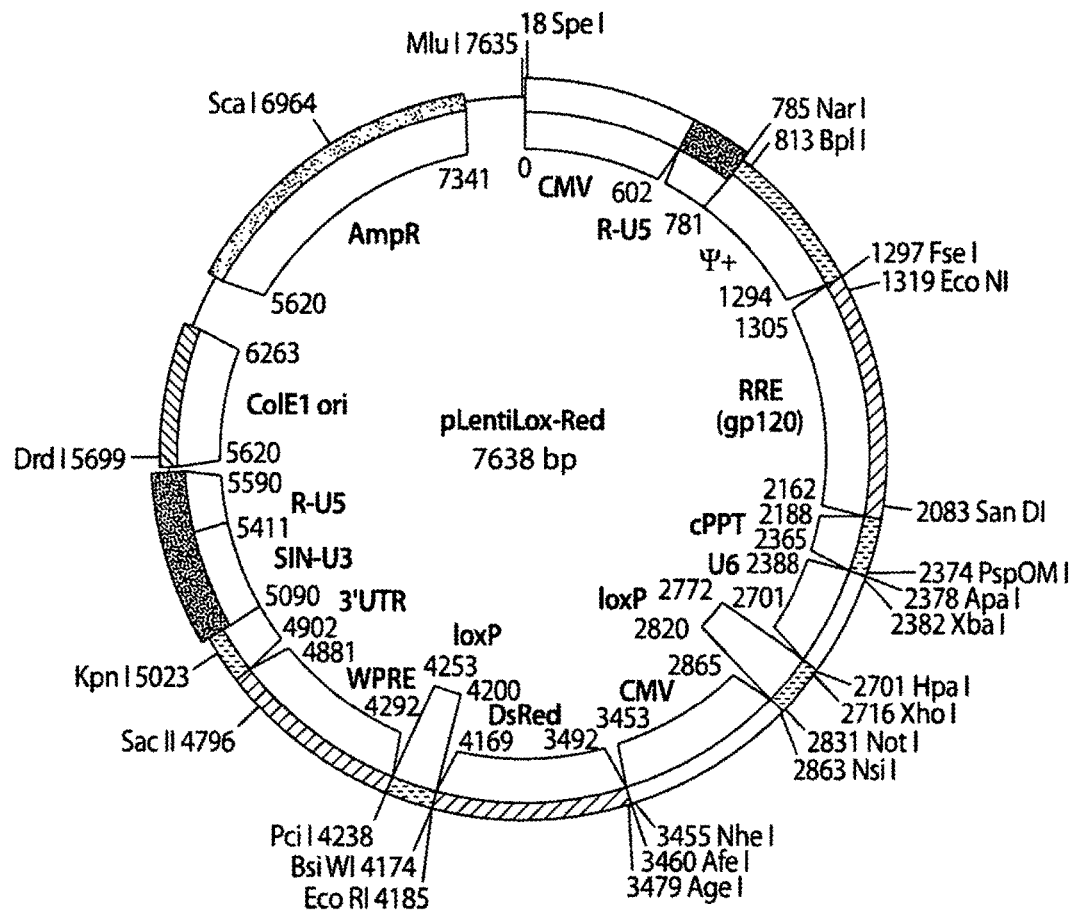

In this embodiment, a polymerase chain reaction (PCR)-mediated method for generating U6 promoter-driven cassettes for expression of hairpin-loop siRNAs (FIG. 3) was employed. A 5' primer that hybridizes to the 5' end of the U6 promoter, and a long 3' primer that hybridizes to the 3' end of the same promoter and also includes a long extension that encodes the hairpin cassette and terminator sequence are used (FIG. 4).

Other methods readily available to one of ordinary skill in the art, including construction of dual transgene cassettes each encoding a single strand of the duplex siRNA, are also possible and are not excluded by examples herein.

Example 4

Construction and Production of Lentivirus Vectors Expressing Inhibitory Sequences In this embodiment, for long-term suppression of HLA expression, third-generation self-inactivating HIV-based lentivirus vectors are constructed and produced for efficient and long-term gene delivery of the siRNA cassettes.

The life cycle of lentiviruses is similar to that of oncoretroviruses, which have been employed extensively as gene transfer vectors, however there are several major differences. Vectors based on oncoretroviruses such as Moloney murine leukemia virus (MLV), which have hitherto been the most popular gene delivery system used in clinical trials, can transduce only cells that divide shortly after infection, because the MLV pre-integration complex cannot migrate to the nucleus in the absence of nuclear envelope breakdown during mitosis. In contrast, lentiviruses such as HIV can infect non-proliferating cells, owing to the karyophilic properties of the lentiviral pre-integration complex which allows recognition by the cell nuclear import machinery.

Correspondingly, HIV-derived vectors can transduce cell lines that are growth-arrested in culture, as well as primary hematopoietic stem cells and terminally differentiated primary cells including neurons, hepatocytes, cardiomyocytes, endothelium, alveolar pneumocytes, and keratinocytes. Once nuclear entry by the lentiviral vector has occurred, the reverse-transcribed vector sequence is permanently integrated into the host cell genome, thereby achieving long-term stable transgene expression.

Lentiviral vectors are generally pseudotyped (i.e., encoated with a heterologous envelope protein) with vesicular stomatitis virus glycoprotein (VSV-G) to achieve wider host range and stability of virions. Recently, HIV-derived multiply attenuated vector systems deleted of the accessory genes vif, vpr, vpu, nef and tat have been reported (Zufferey et al., 1997; Dull et al., 1998). The only auxiliary gene remaining in this system is therefore rev, which, along with the Rev response element (RRE) as its cognate binding sequence, is required for efficient export of the vector and packaging construct RNAs from the nucleus during virus production. Thus both toxicity as well as the likelihood of recombination are reduced in these second- and third-generation lentiviral vector systems, which are now generally (commercially available, for example, from Invitrogen, Inc., Carlsbad, Calif. as the Virapower kit) available and readily used by one of ordinary skill in the art.

Another advantage of lentiviral vector systems is that the endogenous promoter in the HIV long terminal repeat (LTR) depends on the HIV-encoded Tat transctivator protein for transcriptional function. As the sequences encoding Tat are completely removed from the lentiviral vector construct used herein, there is little promoter activity from the LTR, and effective transgene expression is dependent on the addition of an internal promoter. Although most lentiviral constructs currently contain internal CMV promoters to drive transgene expression, this dependence on internal promoters is advantageous for control of expression, for example, expression that is tissue-specific or conditional (e.g., tetracycline-responsive) promoters. Internal promoters may also be important for long-term gene expression, as silencing of CMV promoter-driven transgene expression over time in some lines of cells is avoided or eliminated. Furthermore, it has previously been found that, despite the lack of significant promoter activity in the absence of Tat, promoter interference between the HIV LTR and the internal CMV promoter can occur, thus significantly attenuating the levels of transgene expression achieved. This has been largely overcome by the use of third-generation self-inactivating (SIN) vectors, in which a portion of the U3 region of the 3' LTR has been deleted; thus, after reverse transcription, this deletion will be copied to the 5' LTR and hence result in loss of LTR promoter sequences in the integrated provirus, which therefore prevents interference with the function of the internal promoter.

An HIV-based packaging system for the production of lentiviral vectors is employed; such packaging systems are now commercially available, and any suitable system can be utilized for this method. In this example, a packaging system consisting of the following plasmid-based constructs is employed: lentivirus packaging construct pCMVΔR8.91, which contains the HIV gag-pol genes driven by a CMV promoter, with both the packaging signal and most of the env gene deleted (except for the RRE and the Tat and Rev coding sequences), and is deleted of vif, vpr, vpu, and nef, envelope construct pCMV-VSVG, encoding the vesicular stomatitis virus glycoprotein (VSV-G) envelope, which allows efficient transduction of a wide variety of cell types, as the receptor for VSV-G is thought to be phospholipids; and the vector construct pRRLsinCMVGFPpre, which contains a 5' LTR in which the HIV promoter sequence has been replaced with that of Rous sarcoma virus (RSV), a self-inactivating 3' LTR containing a deletion in the U3 promoter region, the HIV packaging signal, RRE sequences linked to a marker gene cassette consisting of the *Aequora* jellyfish green fluorescent protein (GFP) driven by the CMV promoter, and the woodchuck hepatitis virus PRE element, which appears to enhance nuclear export. Presence of the GFP marker gene allows quantitation of transduction efficiency by direct UV fluorescence microscopy or flow cytometry.

The PCR product encoding the U6 promoter-siRNA hairpin loop cassette was inserted into the multiple cloning site upstream of the CMV-GFP sequence in the vector by recombinant plasmid cloning methods, and the vector was sequenced to confirm successful insertion. The pRRLsin-U6siRNA-CMVGFP vector construct was then transiently co-transfected along with the pCMVΔR 8.91 gag-pol packaging construct and pCMV-VSV-G env construct into 293T cells to produce virus. This transient transfection system resulted in high level expression of viral proteins and efficient packaging of vector genomes without the need for long-term maintenance of stable packaging cell lines and thus without the attendant risk of recombination leading to generation of helper virus over time. The virus supernatants were harvested, filtered sterilized through a 0.45 .mu.m syringe filter, and used to transduce donor graft cells.

Example 5

Inhibition of Expression of HLA Antigens: β2 Microglobulin Subunit Suppression

Lentivirus vectors, which readily infect quiescent non-dividing cells, are capable of highly efficient gene transfer to a wide variety of primary human cell types, including hematopoietic progenitor cells, as well as a variety of differentiated cells. In this example cells were infected, and accordingly transduced: several cell types including primary cardiomyocytes (FIG. 6A), alveolar (primary lung) epithelium (FIG. 6B), primary human keratinocytes (FIG. 7), and others. Furthermore, as a result of the methods and vectors used herein, permanent integration into the genome of the host cell was achieved.

Figure 6A:
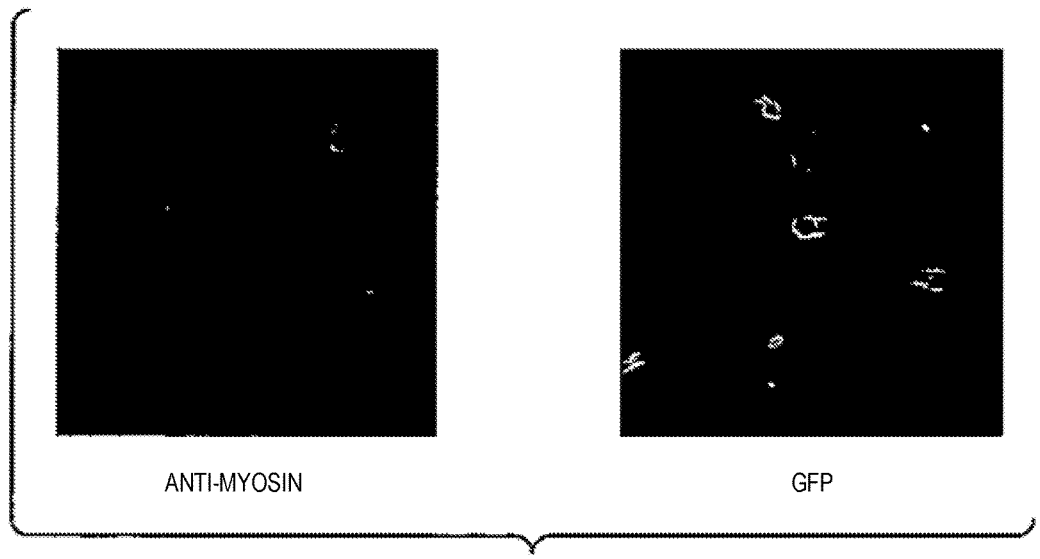
FIG. 6A is a set of photographs showing high efficiency transduction of primary cardiomyocytes with VSV-G pseudotyped lentivirus vectors as determined by anti-myosin staining (left) and green fluorescent protein (GFP) fluorescence determined by fluorescence activated cell sorting (FACS; right).
Figure 6B:
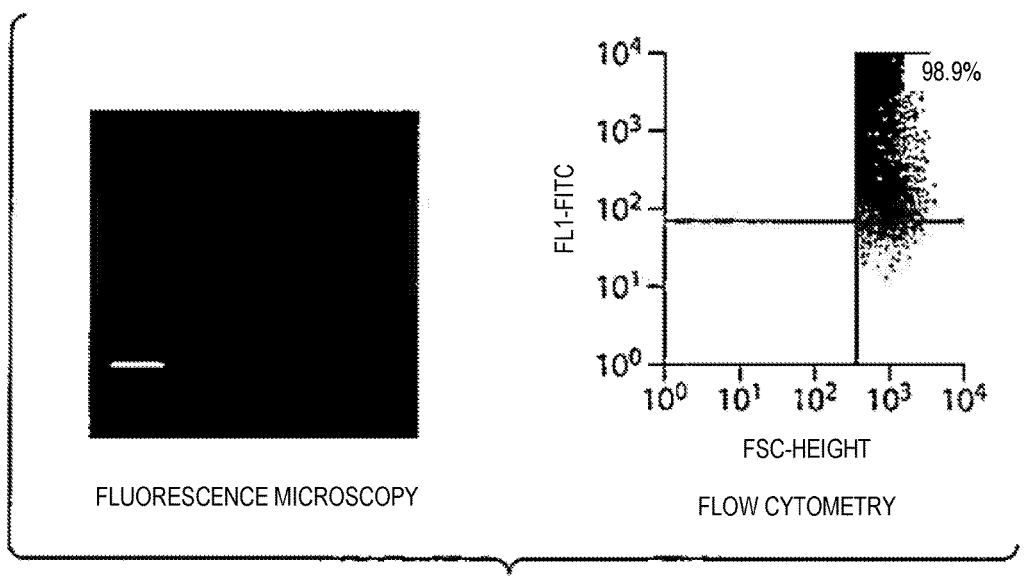
FIG. 6B is a set of photographs showing high efficiency transduction of primary lung epithelial cells with VSV-G pseudotyped lentivirus vectors as determined by fluorescence microscopy (left) and flow cytometry (FACS; right). Flow cytometry data show that 98.9% of cells were successfully transduced.
Figure 7:
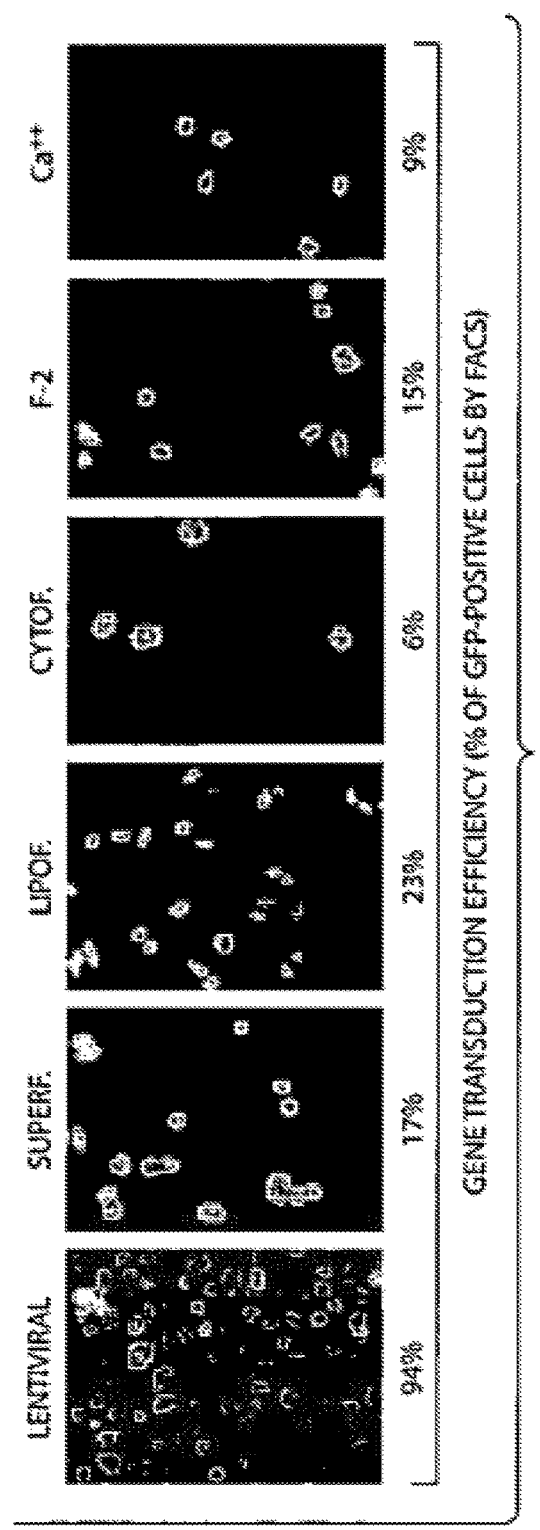
FIG. 7 is a set of photographs showing higher transduction efficiencies (94%) achieved by lentivirus vectors (left) in primary human keratinocytes than by conventional transfection, including superfection (17%), lipofection (23%), cytofection (6%), F-2 (15%), and Ca$^{++}$ (9%), each transduction efficiency measured by % GFP-positive cells by fluorescence activated cell sorting (FACS).

Data in FIG. 6A shows that high efficiency transduction of primary cardiomyocytes with VSV-G pseudotyped lentivirus was achieved. All of the anti-myosin staining cells (left panel) also show expression of GFP (right panel). Further, as shown in FIG. 7, lentivirus vectors achieved higher transduction efficiencies (94% of cells were GFP positive in a FACS assay) in primary human keratinocytes than any of the conventional transfection methods used as controls (efficiencies from 6 to 23%).

In this example, siRNA-encoding lentivirus vectors were employed to obtain inhibition of expression of β2 microglobulin in human cells. The lentivirus vector preparation was incubated with the target cell population in culture (human 293 embryonic kidney cells) overnight at a multiplicity of infection (MOI) of 10, and the medium was replenished the following day. After 48 hours, viral transgene expression was confirmed by flow cytometric detection of the linked green fluorescent protein (GFP) reporter.

As the lentiviral vector permanently integrates into the target cell genome, achieving stable expression of the siRNA, progressive and constitutive inhibition of β2 microglobulin was demonstrated by flow cytometry at any time thereafter once existing pools of already synthesized β2 microglobulin (β2-MG) protein have turned over. In this case as shown in FIG. 8, a phycoerythrin (red fluorescence)-labeled anti-β2 microglobulin antibody was employed to examine the levels of cell surface β2 microglobulin in the transduced (left-shifted curve) compared to control cells that were transfected with mock empty vector, i.e., untransduced cells. These data show that the lentivirus-mediated gene transfer of hairpin siRNA achieved inhibition of human β2-MG.

An embodiment of methods herein is use of siRNA-encoding lentivirus vectors for suppression, in preparation of donor cells for the purpose of graft to a recipient subject, of HLA antigens in hematopoietic progenitors from bone marrow, peripheral blood stem cells, or umbilical cord blood stem cells.

Cells are harvested from the donor, cultured ex vivo under standard cell culture conditions in presence of hematopoietic growth factors, and incubated with siRNA-encoding lentivirus vectors as above. As previously, siRNA-mediated loss of HLA cell surface expression was monitored by flow cytometry, and additionally, the functional loss of immune responses by recipient lymphocytes was monitored by mixed lymphocyte reaction (MLR) and chromium lysis assays, which are well-established immunological methods to determine immunoreactivity against target cells.

Bone marrow transplantation by standard procedures is then performed using the lentivirus-transduced cells confirmed to show loss of HLA expression and showing non-reactivity in the immunological assays.

In other embodiments, lentivirus-mediated gene transfer of siRNA sequences is used for reduction of graft immunogenicity by similar lentivirus-mediated siRNA treatment of other donor cells, including but not limited to pancreatic islet cell transplants, hepatocyte transplants, and cornea transplants. For solid organ transplants including kidney, lungs, and heart, siRNA-lentivirus preparations are perfused into the in-flowing arterial vasculature of the organ, as well as via intraurethral (in the case of the kidney), intracoronary (in the case of the heart), and intratracheal (in the case of the lungs) routes, prior to cryopreservation.

Example 6

Inhibition of Expression of HLA Antigens: Suppression of Each of HLA Class I MHC A, B and C Alleles, and Suppression of Class I MHC A Only The gene encoding the a subunit of the class I MHC protein is organized similarly for each of the A, B and C alleles. Exon 1 encodes a signal peptide; exon 2 encodes the α1 domain; exon 3 encodes the α2 domain; exon 4 encodes the α3 domain; exon 5 encodes a transmembrane region; exons 6 and 7 encode cytoplasmic domains and are alternatively spliced; and exon 8 is untranslated. Thus a substantial length of genetic material is available to obtain sequences that are unique to each of the A, B and C alleles within the genome, and other sequences that are unique to all three of these alleles in the genome, for suppression by siRNA or antisense techniques of expression of each allele alone, or of expression of all three alleles simultaneously.

Using the strategy described for β2-MG above, sequences that are unique to class I MHC protein A allele (A2-1, SEQ ID NOs:17 and 18 for forward and reverse, respectively; A2-2, SEQ ID NOs:19 and 20 for forward and reverse, respectively; A2-3, SEQ ID NOs:21 and 22 for forward and reverse, respectively; and A2-4, SEQ ID NOs: 23 and 24 for forward and reverse, respectively) or are universal among A, B and C alleles (ABC-1, SEQ ID NOs: 25 and 26 for forward and reverse, respectively; ABC-2, SEQ ID NOs: 27 and 28 for forward and reverse, respectively; ABC-3, SEQ ID NOs: 29 and 30 for forward and reverse, respectively; and ABC-4; SEQ ID NOs: 31 and 32, respectively) were sought and identified as described by the methods herein.

The nucleotide sequences of these oligonucleotide sequences obtained from the A allele and from all of A, B and C alleles of class I MHC HLA ("universal") are shown in Table 3, and the alignment of most common alleles of each of human MHC class I loci mRNA sequences, HLA A*020101, B*070201 and Cw*070101 are shown in Table 4 (SEQ ID NOs: 33, 34 and 35, respectively).

Cells were co-transfected as analyzed for suppression of the class I MHC HLA proteins as above. As shown in FIGS. 9-11, inhibition of expression of class I MHC HLA allele A was observed using the A-specific hairpin siRNA or by using the siRNA with a hairpin common to all three alleles, as was inhibition of expression of all three alleles achieved using the latter siRNA.

As shown in FIG. 12, substantial shifts in cells to a non-expressing condition is found following transduction with the siRNA containing LentiLox-Red vector (lower middle and right panels), stained either with anti-A-2 antibody (middle panels) or with antibody that recognizes all of A, B and C loci (right panels).

These data show that in vivo, siRNA can reduce expression of antigenic determinants on the surface of cells used as donors for the purposes of grafting into recipient subjects, prior to such grafting.

Example 7

Transducing Pancreatic Islet Cells with a Lentivirus Vector for Treating Diabetes Approaches to treating diabetes include grafts of islet cells, obtained for example from cadavers, however additional sources can be used such as cultures of islet or kidney tubule cells differentiated and amplified in cell culture under the influence of a variety of growth factors.

Cells are analyzed for HLA mismatches within the graft cells or in the recipient or between the donor and recipient, and are accordingly treated with the appropriate lentivirus vectors carrying siRNA or antisense as described herein and are subsequently administered to a diabetic or pre-diabetic subject. The diabetic or pre-diabetic subject is afflicted with any form including type I or type II diabetes.

ADDITIONAL REFERENCES CITED

1. Cecka J M. In: Visuals of the clinical histocompatibility workshop 2003. In, Terasaki P I (editor) Canoga Park Calif.: One Lamdba, Inc; 2003. pp 84-85.
2. Rebellato L M et al. Transplantation 2002, 74(11): 1634-6.
3. Meier-Kriesche H U et al. Transplantation 2001, 71(3) 398-401.
4. Terasaki P I. In: Clinical Transplants 2000; Cecka J M, Terasaki P I (editors). Los Angeles Calif.: UCLA Immunogenetics Center; 2000. pp 497-514.
5. Crowe D O. Clinical Transplant 2003, Suppl 9:13-6.
6. Duquesnoy R J et al. Transplantation 2003, 75 (6):884-9.
7. Mandal A K et al. Transplantation 2003, 75(4):494-500.
8. Cecka, J M. In: Clinical Transplants 2001; Cecka J M, Terasaki P I (editors). Los Angeles Calif.: UCLA Immunogenetics Center; 2001. pp 1-18.
9. Opelz G. Human Immunology 2000, 61(2):115-9.
10. Laux G et al. Transplantation 2003, 75 (9):1527-32.
11. Gruessner A C et al. Clinical Transplant 1999, 51-69.
12. Mancini M J et al. Clinical Nephrology 2002, 57 (1): 27-37.
13. Gruber S A et al. Transplantation 2000, 70 (2): 388-91.
14. Rerolle J P et al. Nephrol Dialysis Transplant 2002, (5):905-9.
15. Petruzzo P et al. Diabetes Metab 2000, (3): 215-8.
16. Pelletier R P et al. Am J. Transplant 2002, (2):134-41.
17. Chen M et al. Transplant Proc 1994, 26 (5): 2695.
18. O'Grady J G et al. Lancet 1988; 2(8606):302.
19. Neumann U P et al. Transplantation 2003, (75) 132-137.
20. Sugawara Y et al. Liver Transplantation 2001, (9):769-73.
21. Neumann U P et al. Clin Transplant 2002, (2):122-9.
22. Tillman H L et al. Gut 2001, 48(5):714-9.
23. Muro M et al. Hum Biol 2001, 73(6):845-54.
24. Suh K S et al. Liver Transplant 2002, 8 (12):1109-13.
25. Opelz G et al. N Engl J Med 1994, 330 (12):816-9.
26. Opelz G et al. Rev Immunogenet 1999, 1(3):334-42.
27. Hosenpud J D et al Circulation 1996, 94(2):170-4.
28. Taylor C J et al. Transplantation 1997, 63(9):1346-51.
29. Goffinet J et al. Heart Lung 2002, 31(2):122-30.
30. John R et al. J Thorac Cardiovasc Surg 2003, 125(3): 578-91.
31. Tambur A R et al. Transplantation 2000, 70(7):1055-9.
32. Mehra M R et al. Current Opinion Cardiol 2003, 18(2) 153-8.
33. Lila N et al. Circulation 2002, 105(16):1949-54.
34. Holweg C T et al. Transplantation 2002, 73(8):1353-6.
35. Sundaresan S et al. Transplantation 1998, 65(5):648-53.
36. Quantz M A et al. J. Heart lung Transplant 2000, 19(5):473-9.
37. van den Berg J W et al. Transplantation 2001, 71(3): 368-73.
38. Schulman L L et al. Amer J Respir Crit Care Med 2001, 163(2):437-42.
39. Chalermskulrat W et al. Chest 2003, 123(6):1825-31.

40. Reznik S L et al. J Thoracic Cardiovasic Surgery 2000, 119(1):39-45.
41. Palmer S M et al. Transplantation 2002, 74 (6):799-804.
42. Sharples L D et al. J Heart Lung Transplant 2002, 21(2): 271-81.
43. Jaramillo A et al. Transplantation 2001, 71(7):966-76.
44. Haramillo A et al. Hum Immunol 2003, 64(5):521-9.
45. Lu K C et al. J Heart Lung Transplant 2003; 22(1):35-43.
46. Lu K C et al. Transplantation 2002, 74(9):1297-302.
47. Rubinstein P. N Engl J Med 2001, 345:1842-44.
48. Fleischauer K et al. N Engl J Med 1990; 323:1818-22.
49. Petersdorf E W et al. N Eng J Med 2001; 345:1794-800.
50. Hasegawa W et al. Hematology 2003, 8(1):27-33.
51. Filipovich A H et al. Blood 2001, 97(6):1598-603.
52. van der Meer A et al. Transplantation 2001, 72(5):923-9.
53. Cavet J et al. Blood 2001, 98(5):1594-600.
54. Hahn A B et al. Transplantation 1995, 59:21-27.
55. Bartels M C et al. Br J Ophthalmol 2001, 85(11):1341-6.
56. Volker-Dieben H J et al. Transplantation 2000, 70(4): 640-8.
57. Cicciarelli J et al. Clin Transplant 1992, 6:159-164.
58. Monteiro F et al. Transplantation Proc 1997, 29:1433-1434.
59. El-Awar N et al. Transplant Proc 2002, 34:2531-2532.
60. Patel R et al. N Eng J Med 1969, 280:735-739.
61. Scornik J C et al. Transplantation 1992, 54: 61-64.
62. Higuchi M L et al. Arq Bras Cardiol 1989, 52:39-41.
63. Crespo M et al. Transplantation 2001, 71:652-658.
64. Mauiyyedi S et al. J Am Soc Nephrol 2002, 13:779-787.
65. Watschinger B et al. J Am Soc Nephrol 2002, 13:2420-2423.
66. Piazza A et al. Transplantation 2001, 71:1106-1112.
67. Terasaki P I. Am J of Transplantation 2003, 3:665-673.

TABLE 1

Human β2-Microglobulin siRNA candidate sequences evaluated for similarity in genome

| query_pos | query_sequence_with_pattern | type | gc % | hit_name | alignment | | |
|---|---|---|---|---|---|---|---|
| 106-128 | gagaatggaaagtcaaatttcct (SEQ ID NO: 1) | B, C, D, F | 30 | *Homo sapiens* microtubule-associated protein 6 (MAP6), mRNA (SEQ ID NO: 36) | 3<br>3015 | aatggaaagtcaaatt<br>\|\|\|\|\|\|\|\|\|\|\|\|\|\|\|\|<br>aatggaaagtcaaatt | 18<br><br>3000 |
| 106-128 | gagaatggaaagtcaaatttcct (SEQ ID NO: 1) | B, C, D, F | 30 | *Homo sapiens* myelin gene expression factor 2 (MEF-2), mRNA (SEQ ID NO: 37) | 1<br>1591 | agaatggaaagtcaaa<br>\|\|\|\|\|\|\|\|\|\|\|\|\|\|\|\|<br>Agaatggaaagtcaaa | 16<br><br>1606 |
| 106-128 | gagaatggaaagtcaaatttcct (SEQ ID NO: 1) | B, C, D, F | 30 | *Homo sapiens* prokineticin 2 (PROK2), mRNA (SEQ ID NO: 38) | 2<br>1048 | gaatggaaagtcaaatt<br>\|\|\|\|\|\|\|\|\|\|\|\|\|\|\|\|<br>gaatggaaagccaaatt | 18<br><br>1064 |

TABLE 3

```
Sequences specific to the A locus of human MHC I that were chosen for targeting
with siRNAs
(The A*020101 allele was chosen for targeting from among all of the A locus
alleles because it is the most frequent in the caucasian population).
A2-1:   GGATTACATCGCCCTGAAAG         (SEQ ID No: 7)
A2-2:   GCAGGAGGGTCCGGAGTATT         (SEQ ID No: 8)
A.2-3   GGACGGGGAGACACGGAAAG         (SEQ ID No: 9)
A2-4:   GAAAGTGAWIJGGCCCACTCA        (SEQ ID No: 10)

Sequences common to the most frequent* alleles of the human MHC I A, B and C loci
that were chosen for targeting with siRNAs
(*most frequent in the caucasian population)
ABC-1:  GATACCTGGAGAACGGGAAG         (SEQ ID No: 11)
ABC-2:  GCTGTGGTGGTGCCTTCTGG         (SEQ ID No: 12)
ABC-3:  GCTACTACAACCAGAGCGAG         (SEQ ID No: 13)
ABC-4:  GTGGCFCCGCAGATACCTG          (SEQ ID No: 14)

DNA oligos inserted into lentiviral vector to express siRNA hairpins targeting
sequences above
All oligos are shown 5' to 3' and the MHC I sense and antisense sequences are underlined. The region
between the underlined sequences corresponds to the loop of the siRNA hairpin. We used two loop
sequences - either a 9-bp loop (TTCAAGAGA, SEQ ID No; 15) described by Brummelicamp et al [Science,
296(5567):550-3], or an 11-bp loop (GTGTGCTGTCC, SEQ ID No: 16) described by Miyagishi [J Gene
Med. 6(7):715-723]. in some cases, the loop sequence and targeting sequence overlap. The TTTTTT
sequence at the end of each "forward" oligo is for termination of siRNA transcription.

Oligos for A-specific locus targeting
A2-1
forward: TGGATTACATCGCCCTGAAAGTGTGCTGTCCTTTCAGGGCGATGTAATCCTTTTTTC (SEQ ID No: 17)
reverse: TCGAGAAAAAAGGATTACATCGCCCTGAAAGGACAGCACACTTTCAGGGCGATGTAATCCA (SEQ ID No: 18)

A2-2
forward: TGCAGGAGGGTCCGGAGTATTCAAGAGAATACTCCGGACCCTCCTGCTTTTTTC (SEQ ID No: 19)
reverse: TCGAGAAAAAAGCAGGAGGGTCCGGAGTATTCTCTTGAATACTCCGGACCCTCCTGCA (SEQ ID No: 20)

A2-3
forward: TGGACGGGGAGACACGGAAAGTGTGCTGTCCTTTCCGTGTCTCCCCGTCCTTTTTTC (SEQ ID No: 21)
reverse: TCGAGAAAAAAGGACGGGGAGACACGGAAAGGACAGCACACTTTCCGTGTCTCCCCGTCCA (SEQ ID No: 22)
```

TABLE 3-continued

```
A2-4
forward: TGAAAGTGAAGGCCCACTCATTCAAGAGATGAGTGGGCCTTCACTTTCTTTTTC (SEQ ID No: 23)
reverse: TCGAGAAAAAGAAAGTGAAGGCCCACTCATCTCTTGAATGAGTGGGCCTTCACTTTCA (SEQ ID No: 24)

Oligos for targeting all three MHC I loci
ABC-1
forward: TGATACCTGGAGAACGGGAAGTGTGCTGTCCTTCCCGTTCTCCAGGTATCTTTTTC (SEQ ID No: 25)
reverse: TCGAGAAAAAGATACCTGGAGAACGGGAAGGACAGCACACTTCCCGTTCTCCAGGTATCA (SEQ ID No: 26)

ABC-2
forward: TGCTGTGGTGGTGCCTTCTGGTGTGCTGTCCCAGAAGGCACCACCACAGCTTTTTC (SEQ ID No: 27)
reverse: TCGAGAAAAAGCTGTGGTGGTGCCTTCTGGGACAGCACACCAGAAGGCACCACCACAGCA (SEQ ID No: 28)

ABC-3
forward: TGCTACTACAACCAGAGCGAGTGTGCTGTCCTCGCTCTGGTTGTAGTAGCTTTTTC (SEQ ID No: 29)
reverse: TCGAGAAAAAGCTACTACAACCAGAGCGAGGACAGCACACTCGCTCTGGTTGTAGTAGCA (SEQ ID No: 30)

ABC-4
forward: TGTGGCTCCGCAGATACCTGGTGTGCTGTCCCAGGTATCTGCGGAGCCACTTTTTC (SEQ ID NO: 31)
reverse: TCGAGAAAAAGTGGCTCCGCAGATACCTGGGACAGCACACCAGGTATCTGCGGAGCCACA (SEQ ID NO: 32)
```

---

The invention claimed is:

1. A kit for altering allogeneic human cells for a human recipient, the kit comprising:
   a set of lentivirus vectors wherein each of the lentivirus vectors expresses a sequence targeting a consensus conserved nucleic acid sequence, which when expressed in cells, functions as a negative modulator for nucleic acid encoding a domain having a mismatch in an HLA protein and wherein the set of lentivirus vectors comprises individual lentivirus vectors that correspond to individual HLA mismatches for a set of HLA mismatches that consist of HLA Class I mismatches and at least one HLA Class II mismatch;
   wherein the kit is for treatment of human cells by an appropriate subset of the set of lentivirus vectors based at least in part on a determined subset of the set of HLA mismatches between a human donor and a human recipient or between human cells and a human recipient.

2. The kit of claim 1 wherein the sequence comprises an siRNA sequence.

3. The kit of claim 1 wherein the at least one of the lentivirus vectors comprises a marker gene cassette for expressing a fluorescent protein for detection of cells transduced by the at least one of the lentivirus vectors.

4. The kit of claim 3 comprising another one of the lentivirus vectors constructed without the marker gene cassette.

5. The kit of claim 1 comprising an additional composition formed by contacting the at least one of the lentivirus vectors with cells wherein the additional composition comprises at least some of the contacted cells or a population of cells derived from at least some of the contacted cells.

6. The kit of claim 5 wherein the additional composition comprises one or more additional therapeutic agents.

7. The kit of claim 6 wherein the one or more additional therapeutic agents comprises a member selected from a group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), B vitamins, and hyaluronic acid.

8. The kit of claim 1 comprising lentivirus vector compositions wherein the lentivirus vector compositions each comprise a different level of its respective lentivirus vector.

9. The kit of claim 1 wherein the lentivirus vectors comprise the lentivirus vectors as compositions in a dosage unit form.

10. The kit of claim 9 comprising the dosage unit form being based on an animal model.

11. The kit of claim 1 comprising a range of dosages for the lentivirus vectors that is based at least in part on data obtained from an animal study.

12. The kit of claim 1 wherein the HLA Class I mismatches and the at least one HLA Class II mismatch consists of an HLA-A mismatch, a HLA-B mismatch, a HLA-C mismatch, a HLA-G mismatch, a HLA-DR mismatch, a HLA-DQ mismatch and a HLA-DP mismatch.

13. The kit of claim 1 wherein the treatment of human cells by the appropriate subset of the set of lentivirus vectors comprises at least one permanently integratable lentivirus vector.

* * * * *